US010123758B2

(12) United States Patent
Abdolell et al.

(10) Patent No.: US 10,123,758 B2
(45) Date of Patent: *Nov. 13, 2018

(54) METHODS AND SYSTEMS FOR DETERMINING BREAST DENSITY

(71) Applicant: Densitas Incorporated, Halifax (CA)

(72) Inventors: Mohamed Abdolell, Halifax (CA); Tyna Hope, Toronto (CA); Shiva Zaboli, Toronto (CA); Kaitlyn Tsuruda, Milton (CA)

(73) Assignee: DENSITAS INCORPORATED, Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/898,829

(22) Filed: Feb. 19, 2018

(65) Prior Publication Data

US 2018/0168531 A1 Jun. 21, 2018

Related U.S. Application Data

(63) Continuation of application No. 14/912,965, filed as application No. PCT/CA2014/000629 on Aug. 19, 2014, now Pat. No. 9,895,121.

(Continued)

(51) Int. Cl.
*G06K 9/00* (2006.01)
*A61B 6/00* (2006.01)
(Continued)

(52) U.S. Cl.
CPC ............ *A61B 6/502* (2013.01); *A61B 6/5211* (2013.01); *A61B 6/5252* (2013.01);
(Continued)

(58) Field of Classification Search
CPC .................................. G06K 9/00; A61B 6/00
(Continued)

(56) References Cited

U.S. PATENT DOCUMENTS

| 5,133,020 A | 7/1992 | Giger et al. |
| 5,452,367 A | 9/1995 | Bick et al. |
(Continued)

FOREIGN PATENT DOCUMENTS

| CA | 2921786 A1 | 2/2015 |
| CN | 102549618 A | 7/2012 |
(Continued)

OTHER PUBLICATIONS

Palomares, et al., "Mammographic density correlation with Gail model breast cancer risk estimates and component risk factors", Cancer Epidemiology, Biomarkers and Prevention, 2006; 15(7):1324-1330.

(Continued)

*Primary Examiner* — Abolfazl Tabatabai
(74) *Attorney, Agent, or Firm* — Bereskin & Parr LLP/S.E.N.C.R.L., s.r.l.; Tony Orsi

(57) ABSTRACT

Various embodiments are described herein for methods, devices and systems that can be used to determine a breast density value from an input image of patient's breast. In one example embodiment, the breast density value is calculated by receiving an input image corresponding to the digital mammogram, removing metadata information from the input image to generate an intermediate image, generating a region of interest (ROI) image based on the intermediate image, extracting values for predictor variables based on the metadata information, the intermediate image and the ROI image, and calculating breast density based on the values of the predictor variables. The breast density value is calculated based on a breast density model.

20 Claims, 14 Drawing Sheets

Related U.S. Application Data

(60) Provisional application No. 61/867,753, filed on Aug. 20, 2013.

(51) Int. Cl.

| | | |
|---|---|---|
| *G06K 9/20* | (2006.01) | |
| *G06K 9/46* | (2006.01) | |
| *G06K 9/62* | (2006.01) | |
| *G06T 5/00* | (2006.01) | |
| *G06T 7/00* | (2017.01) | |
| *G06T 7/11* | (2017.01) | |
| *G06T 7/12* | (2017.01) | |
| *G06T 7/136* | (2017.01) | |
| *A61B 6/04* | (2006.01) | |

(52) U.S. Cl.
CPC .......... *A61B 6/5258* (2013.01); *A61B 6/5294* (2013.01); *G06K 9/2054* (2013.01); *G06K 9/4642* (2013.01); *G06K 9/6256* (2013.01); *G06T 5/002* (2013.01); *G06T 7/0012* (2013.01); *G06T 7/11* (2017.01); *G06T 7/12* (2017.01); *G06T 7/136* (2017.01); *G06T 2207/10116* (2013.01); *G06T 2207/20061* (2013.01); *G06T 2207/20081* (2013.01); *G06T 2207/30068* (2013.01)

(58) Field of Classification Search
USPC ....... 382/128, 129, 130, 131, 132, 133, 134; 378/4, 8, 21–27, 37, 901; 604/74, 346; 623/7
See application file for complete search history.

(56) References Cited

U.S. PATENT DOCUMENTS

| | | | |
|---|---|---|---|
| 5,491,627 A | 2/1996 | Zhang et al. | |
| 5,537,485 A | 7/1996 | Nishikawa et al. | |
| 5,622,171 A | 4/1997 | Asada et al. | |
| 5,657,362 A | 8/1997 | Giger et al. | |
| 5,673,332 A | 9/1997 | Nishikawa et al. | |
| 5,729,620 A | 3/1998 | Wang | |
| 5,732,697 A | 3/1998 | Zhang et al. | |
| 5,740,268 A | 4/1998 | Nishikawa et al. | |
| 5,815,591 A | 9/1998 | Roehrig et al. | |
| 5,828,774 A | 10/1998 | Wang | |
| 5,832,103 A | 11/1998 | Giger et al. | |
| 5,917,929 A | 6/1999 | Marshall et al. | |
| 6,014,452 A | 1/2000 | Zhang et al. | |
| 6,035,056 A | 3/2000 | Karssemeijer | |
| 6,075,879 A | 6/2000 | Roehrig et al. | |
| 6,078,680 A | 6/2000 | Yoshida et al. | |
| 6,185,320 B1 | 2/2001 | Bick et al. | |
| 6,198,838 B1 | 3/2001 | Roehrig et al. | |
| 6,263,092 B1 | 7/2001 | Roehrig et al. | |
| 6,266,435 B1 | 7/2001 | Wang | |
| 6,301,378 B1 | 10/2001 | Karssemeijer et al. | |
| 6,404,908 B1 | 6/2002 | Schneider et al. | |
| 6,434,262 B2 | 8/2002 | Wang | |
| 6,477,262 B2 | 11/2002 | Wang | |
| 6,574,357 B2 | 6/2003 | Wang | |
| 6,580,818 B2 | 6/2003 | Karssemeijer et al. | |
| 6,628,815 B2 | 9/2003 | Wang | |
| 6,640,001 B2 | 10/2003 | Roehrig et al. | |
| 6,909,795 B2 | 6/2005 | Tecotzky et al. | |
| 7,054,473 B1 | 5/2006 | Roehrig et al. | |
| 7,072,498 B1 | 7/2006 | Roehrig et al. | |
| 7,146,031 B1 | 12/2006 | Hartman et al. | |
| 7,174,515 B1 | 2/2007 | Marshall et al. | |
| 7,286,695 B2 * | 10/2007 | Romsdahl ............ G06K 9/3233 378/21 |
| 7,298,876 B1 | 11/2007 | Marshall et al. | |
| 7,336,809 B2 | 2/2008 | Zeng et al. | |
| 7,346,202 B1 | 3/2008 | Schneider | |
| 7,359,538 B2 * | 4/2008 | Zeng ..................... G06T 7/0012 128/922 |
| 7,397,937 B2 | 7/2008 | Schneider et al. | |
| 7,477,766 B1 | 1/2009 | Roehrig et al. | |
| 7,616,793 B2 | 11/2009 | Marshall et al. | |
| 7,664,302 B2 | 2/2010 | Snoeren et al. | |
| 7,668,352 B2 | 2/2010 | Tecotzky et al. | |
| 7,668,358 B2 | 2/2010 | Snoeren et al. | |
| 7,672,494 B2 | 3/2010 | Doi et al. | |
| 7,680,315 B2 | 3/2010 | Roehrig et al. | |
| 7,769,216 B2 | 8/2010 | Doi et al. | |
| 7,809,175 B2 | 10/2010 | Roehrig et al. | |
| 7,885,443 B2 | 2/2011 | Zingaretti et al. | |
| 7,889,896 B2 | 2/2011 | Roehrig et al. | |
| 8,634,610 B2 | 1/2014 | Kontos et al. | |
| 8,675,933 B2 | 3/2014 | Wehnes et al. | |
| 8,675,934 B2 | 3/2014 | Wehnes et al. | |
| 9,895,121 B2 * | 2/2018 | Abdolell ................ A61B 6/502 |
| 2003/0174873 A1 | 9/2003 | Giger et al. | |
| 2009/0171236 A1 | 7/2009 | Davies | |
| 2009/0324049 A1 | 12/2009 | Kontos et al. | |
| 2010/0226475 A1 | 9/2010 | Smith et al. | |
| 2011/0052025 A1 | 3/2011 | Highnam et al. | |
| 2011/0206261 A1 | 8/2011 | Huo et al. | |
| 2012/0189175 A1 | 7/2012 | Highnam et al. | |
| 2014/0010429 A1 | 1/2014 | Highnam et al. | |
| 2016/0133033 A1 | 5/2016 | Highnam et al. | |
| 2016/0203600 A1 | 7/2016 | Abdolell et al. | |

FOREIGN PATENT DOCUMENTS

| | | |
|---|---|---|
| EP | 2462561 A1 | 6/2012 |
| EP | 2646980 A2 | 10/2013 |
| EP | 3035850 A1 | 6/2016 |
| GB | 2474319 A | 4/2011 |
| GB | 2516366 A | 1/2015 |
| WO | 2011015818 A1 | 2/2011 |
| WO | 2012072974 A2 | 6/2012 |
| WO | 2012082994 A3 | 6/2012 |
| WO | 2013027120 A2 | 2/2013 |
| WO | 2014195669 A1 | 12/2014 |
| WO | 2015011280 A1 | 1/2015 |
| WO | 2015024099 A1 | 2/2015 |
| WO | 2015077076 A1 | 5/2015 |

OTHER PUBLICATIONS

Byng, et al., "The quantitative analysis of mammographic densities", Physics in Medicine and Biology, 1994; 39:1629-1638.

Tagliafico, et al., "Mammographic density estimation: Comparison among BI-RADS categories, a semi-automated software and a fully automated one", The Breast, 2009; 18(1):35-40.

Hologic, Inc., "B. Administrative Information", QUANTRA software application, prepared Feb. 15, 2012 (6 pages).

Hologic, Inc., QUANTRA—510(k) Submission, prepared Aug. 15, 2008 (5 pages).

Matakina Technology Limited, "510(k) Summary", VOLPARA Imaging Software, prepared Sep. 30, 2010 (12 pages).

International Preliminary Report on Patentability dated Mar. 3, 2016 in corresponding International Patent Application No. PCT/CA2014/000629.

Extended European Search Report dated May 22, 2017 in corresponding EP Patent Application No. 14837309.5.

Mustra, et al., "Breast border extraction and pectoral muscle detection using wavelet decomposition", EUROCON 2009, IEEE, St. Petersburg, Russia; pp. 1426-1433.

Chen, et al., "Improving Mammographic Density Estimation in the Breast Periphery", In: Tingberg, et al., eds., Breast Imaging. Cham: Springer International Publishing; 2016, pp. 469-477. (Lecture Notes in Computer Science; vol. 9699).

Zhou, et al., "Computerized image analysis: Estimation of breast density on mammograms", Met Phys., 2001; 28(6):1056-1069.

Ekpo, et al., "Breast composition: Measurement and clinical use", Radiography, 2015; 21(4):1-10.

Keller, et al., "Preliminary evaluation of the publicly available Laboratory for Breast Radiodensity Assessment (LIBRA) software

(56) References Cited

OTHER PUBLICATIONS tool: comparison of fully automated area and volumetric density measures in a case-control study with digital mammography", Breast Cancer Research, 2015; 17:117 (17 pages).

Li, et al., "Computerized analysis of tissue density effect on missed cancer detection in digital mammography", Computerized Medical Imaging and Graphics, 2006; 30(5):291-297.

Yaffe, "Review—Mammographic density. Measurement of mammographic density", Breast Cancer Research, 2008; 10(3): 209 (10 pages).

Byng, et al., "Automated analysis of mammographic densities", Physics in Medicine and Biology, 1996; 41(5):909-923.

Highnam, et al., "Robust Breast Composition Measurement—VOLPARA", Digital Mammography (Lecture Notes in computer Science), 2010; 6136(2010):342-349.

Jeffreys, et al., "Initial experiences of using an automated volumetric measure of breast density: the standard mammogram form", The British Journal of Radiology, 2006; 79(941):378-382.

Ducote, et al., "Quantification of breast density with dual energy mammography: An experimental feasibility study", Medical Physics, 2010; 37(2):793-801.

Notice of Allowance and Notice of References Cited dated May 25, 2017 in corresponding U.S. Appl. No. 14/912,965.

* cited by examiner

METHODS AND SYSTEMS FOR DETERMINING BREAST DENSITY

CROSS-REFERENCE TO RELATED APPLICATION

This application is a continuation of U.S. patent application Ser. No. 14/912,965, filed Feb. 19, 2016. U.S. patent application Ser. No. 14/912,965 claims the benefit of U.S. Provisional Patent Application No. 61/867,753, filed Aug. 20, 2013 and PCT Patent Application No. PCT/CA2014/000629, filed Aug. 19, 2014. The entire contents of Patent Application No. 61/867,753, PCT Patent Application No. PCT/2014/000629 and patent application Ser. No. 14/912,965 are hereby incorporated by reference.

FIELD

The described embodiments relate to methods and systems for determining breast density, and in particular, to methods and systems for determining breast density from a digital mammogram image of a breast.

BACKGROUND

Breast tissue is composed of fibrous and glandular (fibroglandular) and fatty tissue, where fibroglandular tissue radiologically appears dense on X-ray mammograms and fatty tissue appears lucent. In this context, the term mammographic density, often called breast density, has been used to refer to an estimate of the relative proportion of area that the fibroglandular tissue occupies in the breast tissue as presented in a mammogram.

Women with extremely high mammographic density can have four- to six-times the risk of breast cancer relative to women with predominantly fatty breasts; this may be accounted for by an etiologic effect and/or by a masking effect.

The etiologic effect is reflected in the fact that breast cancers predominantly develop in the epithelial cells that line the ducts of the breast and high mammographic density, which reflects breast composition of predominantly fibrous and glandular tissue, may therefore indicate an increased likelihood of developing breast cancer. The masking effect results from the increased difficulty, and therefore decreased sensitivity, of detecting underlying lesions in mammographically dense regions of a digital mammogram as compared to detecting lesions in fatty regions.

Mammographic density is of particular interest because, unlike most other non-modifiable risk factors (such as age and family history), breast density may be potentially modifiable by therapeutic interventions. An increase in mammographic density over time may be an indicator of elevated breast cancer risk and it has been postulated that a reduction in breast density over time may be related to a decrease in breast cancer risk. Furthermore, the inclusion of mammographic density with other known risk factors may add predictive value in breast cancer risk models and improve individual breast cancer risk predictions.

Breast density has been assessed subjectively using various approaches including categorical scales, Visual Analogue Scales, and semi-automated threshold-based algorithms to describe breast composition in terms of mammographic density.

One such subjective approach is the American College of Radiology (ACR) Breast Imaging Reporting and Data System (BI-RADS) breast composition assessment scale. This scale has been described in numerous studies relating the appearance of mammographic density to breast cancer risk. The ACR BI-RADS scale describes four categories of mammographic breast density and breast composition which radiologists are recommended to use in the evaluation of mammographic density. In some states in the US, the summary of the mammogram report that is sent to patients (sometimes called the lay summary) must contain information about breast density. This information may be worded in lay language instead of using the BI-RADS density lexicon and women whose mammograms show heterogeneously or extremely dense breasts may be told that they have "dense breasts". A major shortcoming of the ACR BI-RADS scale for reporting breast density is that it is reader dependent; it is a subjective estimate of breast density that may be biased and not reliably reproducible.

While the ACR recommends the use of their BI-RADS scale, they acknowledge that many radiologists will use alternative scales for classification of breast composition from X-ray mammograms such as Wolfe grades, Boyd's Six Category Classification, Tabar patterns, and variations of the BI-RADS density scale. Irrespective of which scales are used, subjective assessments of breast density suffer from a common shortcoming of not being reliably reproducible.

SUMMARY

In one aspect, in at least one embodiment described herein, there is provided a method for determining a breast density measurement from a mammogram.

The method generally comprises receiving an input image corresponding to the digital mammogram; removing metadata information from the input image to generate an intermediate image; generating a region of interest (ROI) image based on the intermediate image; extracting values for predictor variables from the metadata information, the intermediate image and the ROI image; and calculating the breast density measurement based on the values of the predictor variables.

While the method generally describes the use of a craniocaudal (CC) or medio-lateral oblique (MLO) view mammograms, this example embodiment of the method, as well as other embodiments of methods described in accordance with the teachings herein, may also be applied to other views such as medio-lateral (ML), latero-medial (LM) and other views known to those skilled in the art.

In some embodiments, the method for determining a breast density measurement further comprises processing the intermediate image to generate a pre-ROI image, wherein the ROI image is generated by processing the pre-ROI image.

In some embodiments, generating the pre-ROI image may comprise resizing the intermediate image.

In some embodiments, generating the pre-ROI image may additionally or alternatively comprise removing noise.

In some embodiments, the noise may be removed by applying smoothing. In some other embodiments, noise removal may include removing salt and pepper noise from the intermediate image. These processes may be linear, non-linear, or a combination thereof.

In at least one embodiment, generating the ROI image may comprise generating an initial breast signal mask from the pre-ROI image by separating tissue from background. The tissue is any soft tissue of the patient's body that is imaged by the mammogram and may comprise breast tissue, muscle, lymph nodes, skin, and other soft tissue.

In some embodiments, generating the ROI image may comprise refining the initial breast signal mask by removing a nipple area from the pre-ROI image. In some cases, the nipple area may be removed by removing the interior part of the nipple area. In some other cases, the nipple area may be removed by removing the exterior part of the nipple area. In some further cases, generating the ROI image may involve removing both the interior and exterior part of the nipple area.

In some embodiments, generating the ROI image may alternatively or additionally comprise refining the initial breast signal mask by removing the pectoral muscles. The pectoral muscles refer to both the pectoralis minor and pectoralis major muscles. In at least one embodiment, the pectoral muscles may be removed by using the Hough transformation.

In some embodiments, generating the ROI image may alternatively or additionally comprise refining the initial breast signal mask to remove the region under the main breast. This region under the main breast may be the chest wall in the MLO view or the adjacent breast in the CC view.

In some embodiments, generating the ROI image may alternatively or additionally comprise refining the initial breast signal mask by removing subcutaneous fat from the breast and skin.

In some embodiments, generating the ROI image may alternatively or additionally comprise refining the initial breast signal mask by removing a portion of the region in front of the pectoral muscles.

In some embodiments, the ROI image may be further refined by smoothing boundaries, filing holes, or other methods of adjusting binary objects known to those skilled in the art.

In some embodiments, the ROI image may be further refined by removing regions that correspond to those that contain detected skin folds in the intermediate image.

The ROI image generated according to the various embodiments disclosed herein comprises a plurality of pixels with either zero or non-zero values. The non-zero values of the ROI image correspond to regions of intermediate image suitable for performing calculations upon.

In at least one embodiment, removing metadata information from the input image comprises removing metadata information from the header of the input image.

In some embodiments, the input image is based on a DICOM standard, and removing metadata information from the input image comprises removing DICOM header information.

In some embodiments, predictor variables from the metadata information may comprise at least one of patient specific parameters, image acquisition device parameters and image acquisition parameters.

In some embodiments, image acquisition parameter may comprise at least one of relative x-ray exposure, exposure duration, laterality, patient orientation and peak kilo-voltage.

In some embodiments, patient specific parameters may comprise at least one of age of the patient, gender of the patient, patient date of birth, and patient identification information.

In some embodiments, image acquisition device parameters may comprise at least one of name and model of the device used to obtain the digital mammogram.

In at least one embodiment, predictor variables may be based on calculations performed on a region of the intermediate image defined by non-zero values of the ROI image. In some other embodiments, calculations may be performed on a region of a processed intermediate image, generated by processing the intermediate image, defined by non-zero values of the ROI image. If the ROI image is derived from a down-sampled version of the intermediate image, the ROI image may be up-sampled or the intermediate image may be down-sampled prior to extracting the features or some other method to ensure correspondence between the pixels of the two images.

In at least one embodiment, predictor variables based on the region of the intermediate or processed intermediate image defined by the non-zero values of the ROI image comprise features describing the histogram of pixel values. In some embodiments, the histogram may be created from the intermediate images, or after processing of the intermediate image has occurred to remove noise or enhance a feature of the image. In some embodiments, the features describing the histogram may comprise at least one of skewness, entropy, maximum between class variance (from a histogram-based automated threshold determination technique), ninety nine percent index and fifty percent index.

In at least one embodiment, predictor variables based on the region of the intermediate or processed intermediate image defined by the non-zero or a subset of non-zero values of the ROI image comprise texture features. In some embodiments, the texture features may comprise at least one of average gradient magnitude value and ratio of edge pixels to the total number of pixels.

In at least one embodiment, measuring values for predictor variables from regions of the intermediate or processed intermediate image defined by non-zero values of the ROI image may comprise measuring values for predictor variables based on relative x-ray exposure, exposure duration, peak kilo-voltage, skewness, entropy, maximum between class variance, ninety nine percent index and fifty percent index, average gradient magnitude value of the region of interest image, average gradient magnitude value of a region within the region of interest image, edge ratio of the region of interest image, edge ratio of a region within the region of interest image, angular second moment (ASM), correlation, entropy and dissimilarity.

In some embodiments, the breast density measurement or value may be calculated based on a breast density model developed based on a regression analysis method, a statistical learning method, or a machine learning method.

In some embodiments, the breast density model may be based on one of regression analysis, linear regression, multiple adaptive regression splines, classification and regression trees, random forests, artificial neural networks, support vector machines and ensemble learning algorithms. Other methods of developing predictor models may be used, as known by those skilled in the art.

In another aspect, in at least one embodiment described herein, there is provided a system for determining a breast density value from a mammogram image of a breast. The system comprises a memory unit; and a processing unit coupled to the memory unit. The processor unit is configured to receive an input image corresponding to the digital mammogram; remove metadata information from the input image to generate an intermediate image; generate a region of interest (ROI) image based on the intermediate image; extract values for predictor variables from the metadata information, the intermediate image and the ROI image; and calculate the breast density measurement based on the values of the predictor variables.

In another embodiment, the processing unit is configured to perform the methods as defined above or other methods in accordance with the teachings herein.

In another aspect, in at least one embodiment described herein, there is provided a computer-readable medium storing computer-executable instructions. The instructions cause a processor to perform a method of determining a breast density value from a mammogram image of a breast, the method comprising: receiving an input image corresponding to the digital mammogram; removing metadata information from the input image to generate an intermediate image; generating a region of interest (ROI) image based on the intermediate image; extracting values for predictor variables from the metadata information, the intermediate image and the ROI image; and calculating the breast density measurement based on the values of the predictor variables.

In some embodiments, the instructions cause the processor to perform the methods as described above or other methods in accordance with the teachings herein.

In some embodiments, the processing system may be located within a hospital, clinic, personal setting or research setting and connected to a Local Area Network (LAN) or a Virtual Local Area Network (VLAN) to receive mammogram images directly from a Picture Archiving and Communication System (PACS), an imager (e.g. the machine that acquires the images) or other systems that acquire and store mammogram images. In some other embodiments, the processing system may be remotely located from the hospital, clinic, or research setting. The images may be received via transfer through the Internet or intranet.

In some embodiments, the processing system and the mammogram image acquisition and storage system are incorporated within a same system, or coupled to each other via a wired or LAN/VLAN connection. In such embodiments, the mammogram images are provided to the processing system through gestures, such as, drag and drop, cut and save, copy and save etc.

In some other embodiments, the processing system and the mammogram image acquisition and storage system are implemented at separate locations. For example, the processing system may be located on a cloud server, and the mammogram image acquisition and storage system may be located in a hospital, clinic, personal setting or research setting. In such embodiments, the mammogram images are uploaded to the cloud server, and the results are downloaded from the cloud server.

In various embodiments, the input images may be assessed for suitability (type, view, etc.) and placed in a queue until processing resources are available. After processing, the calculated values and identifiers may be logged within the system database. The resultant output data may then be sent to one or more input/output devices, such as the PACS, Electronic Medical Record (EMR), mammogram review stations, other Hospital Information Technology (HIT) systems, personal computers (e.g. laptops), and communication devices (e.g. cell phones), etc., in appropriate format. The formats may include DICOM Structured Report (SR), DICOM Secondary Capture (SC), DICOM Greyscale Softcopy Presentation State (GSPS), HL7, xml format, standard computer formats such as portable document format (pdf) or comma separated values (csv), and other formats known to those skilled in the art. The reported values may display automatically at the input/output device or may require user initiation to view.

When reporting the calculated breast density, the images may be grouped by a patient identifier such as a study identifier or similar parameter as is known to those skilled in the art, allowing the calculation and reporting of "summary values". These summary values may include, but are not limited to, an average, a weighted average or some other suitable combination providing values that combine density information to describe density per view, per breast and/or per patient.

In some embodiments, the system may process the mammogram images in clinical or research mode. The processing of the images is not affected by the mode, but rather the mode affects the structure of the output data and the format in which it is delivered. For example, in research mode, the data may be output in a tabular format in a way that allows analysis of a sample of patients within a study. As another example, in clinical mode, the output data may be specific to a single patient and may be presented in a report necessary for the utilization of this data in a clinical environment.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment and which will now be briefly described.

Figure 1A:
FIG. 1A is an example of a mammogram image illustrating a fatty breast with less than or equal to 25% density.

Further aspects and advantages of the embodiments described herein will appear from the following description taken together with the accompanying drawings.

DESCRIPTION OF EXAMPLE EMBODIMENTS

Various apparatuses or processes will be described below to provide an example of at least one embodiment of the claimed subject matter. No embodiment described below limits any claimed subject matter and any claimed subject matter may cover processes, apparatuses, devices or systems that differ from those described below. The claimed subject matter is not limited to apparatuses, devices, systems or processes having all of the features of any one apparatus, device, system or process described below or to features common to multiple or all of the apparatuses, devices, systems or processes described below. It is possible that an apparatus, device, system or process described below is not an embodiment of any claimed subject matter. Any subject matter that is disclosed in an apparatus, device, system or process described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It should also be noted that the terms "coupled" or "coupling" as used herein can have several different meanings depending in the context in which the term is used. For example, the term coupling can have a mechanical or electrical connotation. For example, as used herein, the terms "coupled" or "coupling" can indicate that two elements or devices can be directly connected to one another or connected to one another through one or more intermediate elements or devices via an electrical element, electrical signal or a mechanical element such as but not limited to, a wire or a cable, for example, depending on the particular context.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

The various embodiments of the devices, systems and methods described herein may be implemented using a combination of hardware and software. These embodiments may be implemented in part using computer programs executing on programmable devices, each programmable device including at least one processor, an operating system, one or more data stores (including volatile memory or non-volatile memory or other data storage elements or a combination thereof), at least one communication interface and any other associated hardware and software that is necessary to implement the functionality of at least one of the embodiments described herein. For example, and without limitation, the computing device may be a server, a network appliance, an embedded device, a computer expansion module, a personal computer, a laptop, a personal data assistant, a cellular telephone, a smart-phone device, a tablet computer, a wireless device or any other computing device capable of being configured to carry out the methods described herein. The particular embodiment depends on the application of the computing device.

In some embodiments, the communication interface may be a network communication interface, a USB connection or another suitable connection as is known by those skilled in the art. In other embodiments, the communication interface may be a software communication interface, such as those for inter-process communication (IPC). In still other embodiments, there may be a combination of communication interfaces implemented as hardware, software, and a combination thereof.

In at least some of the embodiments described herein, program code may be applied to input data to perform at least some of the functions described herein and to generate output information. The output information may be applied to one or more output devices, for display or for further processing.

At least some of the embodiments described herein that use programs may be implemented in a high level procedural or object oriented programming and/or scripting language or both. Accordingly, the program code may be written in C, Java, SQL or any other suitable programming language and may comprise modules or classes, as is known to those skilled in object oriented programming. However, other programs may be implemented in assembly, machine language or firmware as needed. In either case, the language may be a compiled or interpreted language.

The computer programs may be stored on a storage media (e.g. a computer readable medium such as, but not limited to, ROM, magnetic disk, optical disc) or a device that is readable by a general or special purpose computing device. The program code, when read by the computing device, configures the computing device to operate in a new, specific and predefined manner in order to perform at least one of the methods described herein.

Furthermore, some of the programs associated with the system, processes and methods of the embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The various embodiments disclosed herein generally relate to improved techniques for the determination of breast density from a digital mammogram image. Visual perception of mammographic density on X-ray mammograms by radiologists is a complex activity that may incorporate the assessment of both the distribution and pattern of mammographic density, in addition to the amount of dense tissue. For accurate measurements, this complexity should be factored in computer-based approaches for measuring density from X-ray mammograms, rather than employing oversimplified physics-based models alone.

Computer-based approaches for measuring breast density are typically founded on physics models of the composition of the breast as well as models of the imaging technology and imaging process, the validity of which may depend on many assumptions. Simplifying assumptions are made to enable physics-based models to compute breast density assessments; however, every simplifying assumption may introduce error and bias in the density estimate.

For example, the conventional image processing technique of applying a threshold is commonly used in the quantification of breast density on an X-ray mammogram. However, this process does not take into account the thickness of the dense breast tissue and forces an artificial and overly strict binary classification of breast tissue. This binary classification is not valid due to the partial volume effect: most pixels are not entirely dense or entirely fatty, however the application of thresholds necessitates that this simplifying assumption is made.

Underlying any method of breast density assessment is the fact that true breast density remains unknown, so the ratio of dense tissue to overall breast tissue estimates generated by physics-based methods alone may intrinsically be no less biased than visual assessments by radiologists despite being designed to objectively provide density measurements.

Visual assessment of percent density by radiologists is strongly associated with breast cancer risk because radiologists incorporate more than just percentage of dense tissue in their breast density assessment. Radiologists also incorporate the distribution, characterization, and other features of parenchymal patterns as presented in mammograms. These additional features captured in visual assessment by radiologists are not captured using physics-based models that only capture a subset of these features. Therefore, physics-based models alone fail to demonstrate the same strength of association with cancer risk that has been observed using visual assessments of breast density.

The various embodiments disclosed herein relate to improved techniques over existing methods as these techniques take into consideration factors such as the physics of image acquisition, image signal content and the human response to the mammogram in order to determine the density. The digital mammogram image for which breast density is determined in the various systems and methods disclosed herein may be any mammogram view. For example, the digital mammogram image may be a cranio-caudal (CC) view, a medio-lateral oblique (MLO) view, a medio-lateral (ML) view, a latero-medial (LM) view or other mammogram views known to those skilled in the art. Various embodiments illustrated herein are discussed with reference to CC and MLO views. However, all concepts are easily translated to the other views.

In various embodiments, an input digital mammogram image for which breast density is determined is a processed raw digital mammogram image, which is a raw or 'for processing' digital mammogram image that has already undergone post-processing methods to enhance image properties. When the enhancement to the raw image has been performed so that the mammogram is intended for viewing by a human observer, such as a radiologist, the images are then designated as "for presentation". The terms "for processing" and "for presentation" are defined by the DICOM standard.

In some embodiments, the 'for presentation' digital mammogram image may be stored in a DICOM (Digital Imaging and Communications in Medicine) standard format. The DICOM standard is a network protocol used for the storage and transmission of medical images, waveforms and accompanying information. In some other embodiments, the 'for presentation' digital mammogram image may be stored in some other format, such as, tiff, jpeg, etc.

In some embodiments, the mammogram image acquisition device and the post-processing methods may be provided by the same manufacturer. In some other embodiments, the mammogram image acquisition device and the post-processing methods may be provided by different manufacturers, parties or companies. In other words, in the latter embodiment, the manufacturer and/or provider of the mammogram image acquisition device, and provider of post-processing methodology and/or devices are separate entities.

The 'for processing' digital mammogram image, from which the 'for presentation' digital mammogram image is generated, is generated from the detected x-rays that have passed through an individual's breast (the individual may be interchangeably referred to as a patient herein).

The teachings herein may be used to standardize breast density estimation without resorting to visual assessments by radiologists. The teachings herein may further be used to generate a quantitative measurement of breast density that is standardized, automated, repeatable, and free of the oversimplifying assumptions that are currently widely made by conventional image processing techniques that implement the application of threshold methods.

Reference is first made to FIGS. 1A-1D, illustrating four categories of mammographic density according to the fourth edition of BI-RADS provided by the ACR. Breasts are made up of a mixture of fibrous and glandular tissues and fatty tissues. Breasts are considered dense if they have a lot of fibrous or glandular tissue but not much fat. Breast density of greater than 50% is commonly referred to as dense. Fatty tissue appears dark on a mammogram and dense tissue appears brighter on a mammogram.

Having dense breast tissue may increase a woman's risk of breast cancer. Dense breast tissue may also make it more difficult for doctors or radiologists to detect cancer on mammograms, since both benign and cancerous lumps/masses in a breast also appear brighter on a mammogram.

Figure 1C:
FIG. 1C is an example of a mammogram illustrating a heterogeneously dense breast composing 51—75% of the breast.
Figure 1B:
FIG. 1B is an example of a mammogram illustrating a breast with scattered areas of fibrograndular density composing 26—50% of the breast.
Figure 1D:
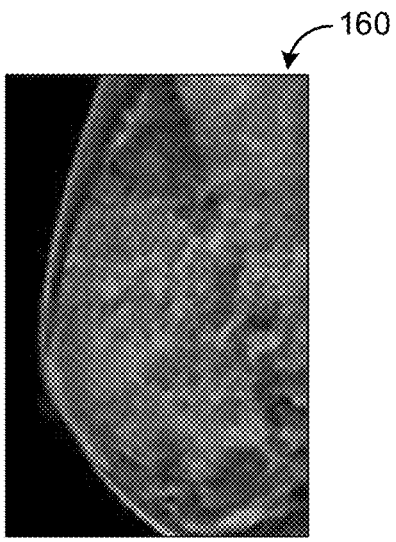
FIG. 1D is an example of a mammogram illustrating an extremely dense breast with greater than 75% density.

FIG. 1A shows a mammogram illustrating a fatty breast 100 with a density of less than or equal to 25%. FIG. 1B shows a mammogram illustrating a breast 120 with scattered areas of fibrograndular density composing 26—50% of the breast. FIG. 1C shows a mammogram illustrating a heterogeneously dense breast 140 composing 51—75% of the breast and FIG. 1D shows a mammogram illustrating an extremely dense breast 160 with a density of greater than 75%.

Figure 2:
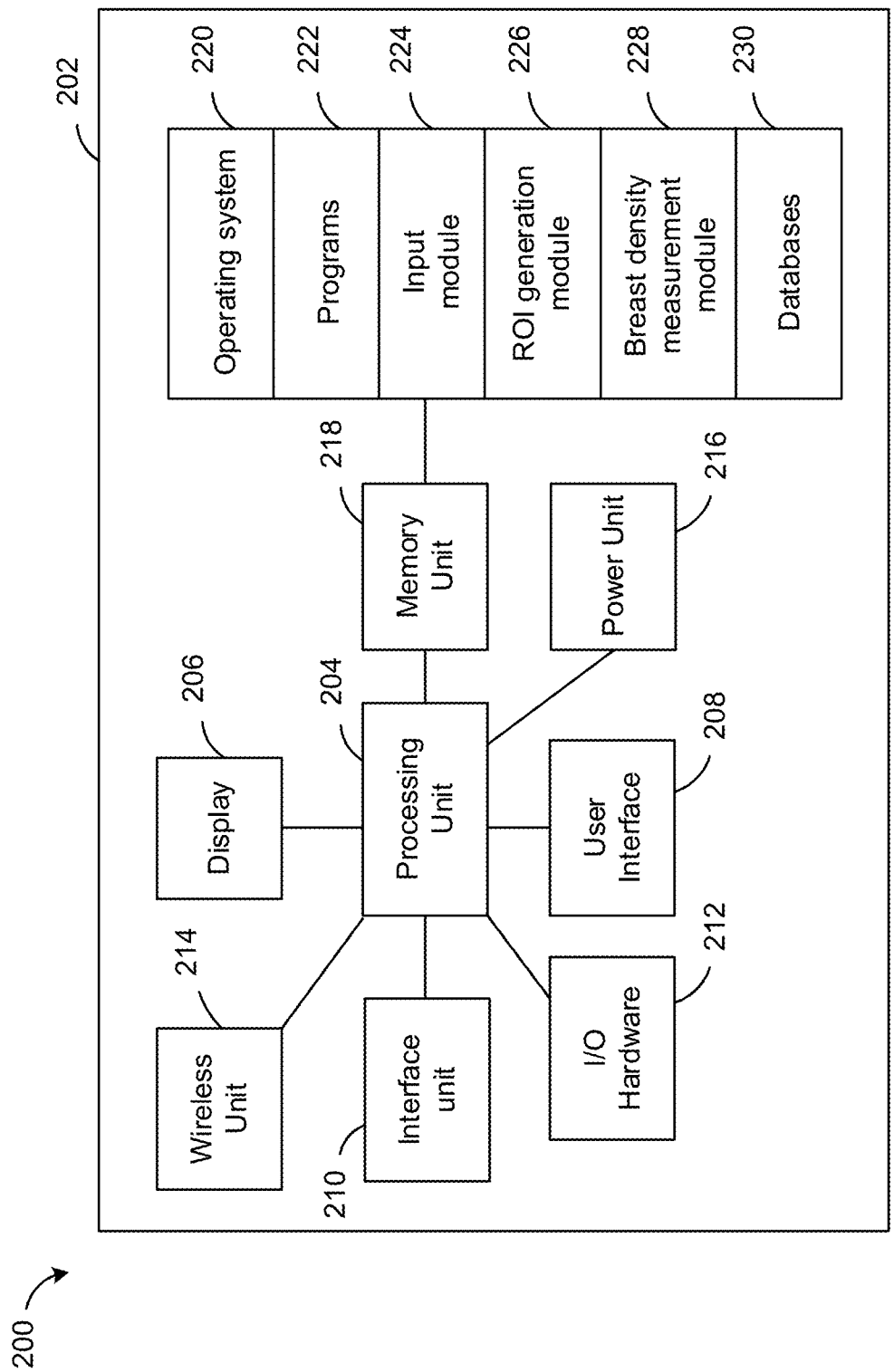
FIG. 2 is a block diagram of a breast density measurement system in accordance with an example embodiment.

Reference is next made to FIG. 2 illustrating a block diagram of a breast density measurement system 200 in accordance with an example embodiment. The system 200 is provided as an example and there can be other embodiments of the system 200 with different components or a different configuration of the components described herein. The system 200 further includes several power supplies (not all shown) connected to various components of the system 200 as is commonly known to those skilled in the art. The breast density measurement system 200 may generally be configured for clinical usage by a PACS administrator (e.g. a "picture archiving and communication system" administrator).

Also illustrated in FIG. 2 is an operator unit 202, which is an interface that is used by a medical practitioner to interact with the breast density measurement system 200 to measure breast density from digital mammogram images of a breast. The operator unit 202 comprises a processing unit 204, a display 206, a user interface 208, an interface unit 210, Input/Output (I/O) hardware 212, a wireless unit 214, a power unit 216 and a memory unit 218. The memory unit 218 comprises software code for implementing an operating system 220, various programs 222, an input module 224, a Region of Interest (ROI) generation module 226, a breast density measurement module 228, and one or more databases 230. Many components of the operator unit 202 can be implemented using a desktop computer, a laptop, a mobile device, a tablet, a server and the like.

The processing unit 204 controls the operation of the operator unit 202. The processing unit 204 can be any suitable processor, controller or digital signal processor that can provide sufficient processing power processor depending on the configuration, purposes and requirements of the operator unit 202 as is known by those skilled in the art. For example, the processing unit 204 may be a high performance general processor. In alternative embodiments, the processing unit 204 can include more than one processor with each processor being configured to perform different dedicated tasks. In alternative embodiments, it may be possible to use specialized hardware to provide some of the functions provided by the processing unit 204.

The display 206 can be any suitable display that provides visual information depending on the configuration of the operator unit 202. For instance, the display 206 can be a cathode ray tube, a flat-screen monitor, an LCD display and the like if the operator unit 202 is a desktop computer. In other cases, the display 206 can be a display suitable for a laptop, tablet or handheld device such as an LCD-based display and the like.

The user interface 208 can include at least one of a mouse, a keyboard, a touch screen, a thumbwheel, a track-pad, a track-ball, a card-reader, voice recognition software and the like again depending on the particular implementation of the operator unit 202. In some cases, some of these components can be integrated with one another.

The interface unit 210 can be any interface that allows the operator unit 202 to communicate with other devices or computers. In some cases, the interface unit 210 can include at least one of a serial port, a parallel port or a USB port that provides USB connectivity. The interface unit 210 can also include at least one of an Internet, Local Area Network (LAN), Ethernet, Firewire, modem or digital subscriber line connection. Various combinations of these elements can be incorporated within the interface unit 210.

The I/O hardware 212 is optional and can include, but is not limited to, at least one of a microphone, a speaker and a printer, for example.

The wireless unit 214 is optional and can be a radio that communicates utilizing CDMA, GSM, GPRS or Bluetooth protocol according to standards such as IEEE 802.11a, 802.11b, 802.11g, or 802.11n. The wireless unit 214 can be used by the operator unit 202 to wirelessly communicate with other devices or computers.

The power unit 216 can be any suitable power source that provides power to the operator unit 202 such as a power adaptor or a rechargeable battery pack depending on the implementation of the operator unit 202 as is known by those skilled in the art.

The memory unit 218 can include RAM, ROM, one or more hard drives, one or more flash drives or some other suitable data storage elements such as disk drives, etc. The memory unit 218 is used to store an operating system 220 and programs 222 as is commonly known by those skilled in the art. For instance, the operating system 220 provides various basic operational processes for the operator unit 202. The programs 222 include various user programs so that a user can interact with the operator unit 202 to perform various functions such as, but not limited to, viewing and manipulating data as well as sending messages as the case may be.

The memory unit 218 may also accept data from one of the input devices, the input module 224, the breast density measurement module 228 and the ROI generation module 226. The memory unit 218 uses the received data to define and store image records. Each image record identifies a digital mammogram image to which the image record relates, such as a processed raw digital mammogram image or a 'for presentation' digital mammogram image. An image record may include measurements for variables that are extracted from the digital mammogram image in its original or processed form. An image record may also include the calculated breast density for the digital mammogram image.

In at least one example embodiment, each image record comprises eighteen entries, where the first entry includes an identifier, such as a name, for the digital mammogram image, the second to seventeenth entries includes measurements for predictor variables, as discussed below, and the eighteenth entry includes the breast density value generated for the corresponding breast image. In some other cases, each image record may include more entries including intermediate and default values.

The input module 224 interacts with at least one of the memory unit 218 and the databases 230 for receiving an input image. The input image may be a processed raw or 'for presentation' digital mammogram image. The input module 224 removes metadata information from the input image to generate an intermediate image. In most cases, the metadata information is removed from the header of the input image. The intermediate image refers to an input image with the header metadata stripped out (i.e. removed) from the input image. In most cases, the intermediate image has a different format than the input image.

The removed metadata information is stored in the memory unit 218 in the image record corresponding to the input image. Removed metadata information may include information such as, but not limited to, patient specific information, image acquisition device information, image acquisition parameters, and other information for example.

The patient specific information may include, but is not limited to, information such as age of the patient, gender of the patient, patient date of birth, and patient identification information. Image acquisition device information may include, but is not limited to, the name, model and/or some other identifier corresponding to the device that was used to carry out the mammogram. Image acquisition parameters may include parameters with the greatest impact on the dose and image quality. Some examples of image acquisition parameters may include, but are not limited to, duration of exposure ("exposure duration"), amount of exposure ("relative x-ray exposure"), peak kilo voltage output of the x-ray generator ("peak kilo-voltage"), laterality of the paired breasts examined ("laterality") and patient orientation, for example.

The ROI generation module 226 interacts with at least one of the memory unit 218 and the databases 230 to process the intermediate image to determine a region of interest. The region of interest refers to a breast tissue region within the intermediate image that allows for more accurate breast density measurements. The ROI generation module 226 determines the region of interest by applying a series of image processing algorithms to the intermediate image. FIGS. 3A to 3J illustrate breast images at various stages due to various image processing methods that may be performed by the ROI generation module 226.

Figure 3A:
FIG. 3A is an example of a down sampled breast image.

In at least some embodiments, the ROI generation module 226 may be configured to down sample the intermediate image to resize the image. For example, the ROI generation module 226 may resize the intermediate image to $1/16^{th}$ of its original size. FIG. 3A illustrates a down sampled breast image 300.

In at least some embodiments, the ROI generation module 226 may be configured to up sample the intermediate image to resize the image. In some further embodiments, no resizing of the intermediate image is carried out.

In at least some embodiments, the ROI generation module 226 may be configured to smooth the intermediate image. The intermediate image may be smoothed either before or after resizing. The intermediate image may be smoothed by using a smoothing filter such as, but not limited to, a Gaussian filter, a box filter, a low-pass filter, or anisotropic diffusion, for example. In some cases, a Gaussian filter with a 7×7 kernel may be used to smooth the intermediate image.

In at least some embodiments, the ROI generation module 226 may be configured to remove salt and pepper noise from the smoothed image. The salt and pepper noise may be removed by applying linear or non-linear filters such as, but not limited to, a Rank detection filter, anisotropic diffusion, or an exponential filter, for example. In some cases, a class of a Rank detection filter, such as, but not limited to, a median filter may be used to remove salt and pepper noise from the smoothed image. In some cases, a median filter with a 3×3 kernel may be used to de-noise the smoothed image, for example.

The resultant image that is then used for processing by the ROI generation module 226 for determining the ROI may be referred to as a pre-ROI image. As described, in some embodiments, the intermediate image may have been at least one of resized, smoothed and de-noised (to remove salt and pepper noise, for example) to generate the pre-ROI image. In some other embodiments, the pre-ROI image may be the same as the intermediate image. In such embodiments, no resizing, smoothing and/or salt and pepper noise removal takes place. In some further embodiments, processes other than resizing, smoothing and salt and pepper noise removal may be applied to the intermediate image to remove noise, unwanted signal, metadata, etc. from the intermediate image to generate the pre-ROI image.

Figure 3B:
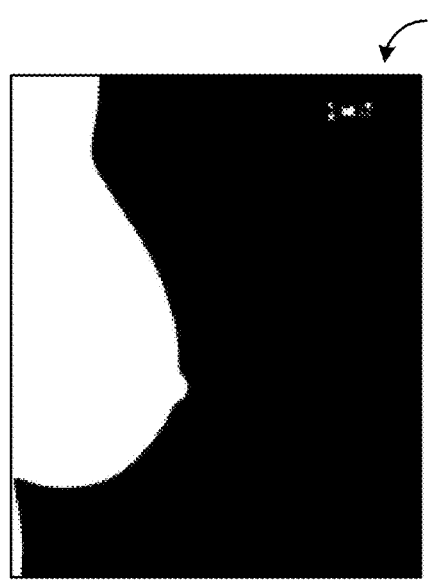
FIG. 3B is an example of a breast signal mask.

The ROI generation module 226 determines the region of interest by generating an initial breast signal mask of the pre-ROI image and then refining the mask. For example, the ROI generation module 226 may process the pre-ROI image to separate the background of the pre-ROI image from the area containing the breast tissue to generate the initial breast signal mask. For example, the ROI generation module 226 may apply a threshold to separate the background from the area containing the tissue. FIG. 3B illustrates a breast signal mask 310.

The ROI generation module 226 may be configured to process the generated initial breast signal mask to remove the exterior part of the nipple in the breast area. The ROI generation module 226 may remove the exterior part of the nipple by using various image processing algorithms.

Figure 3C:
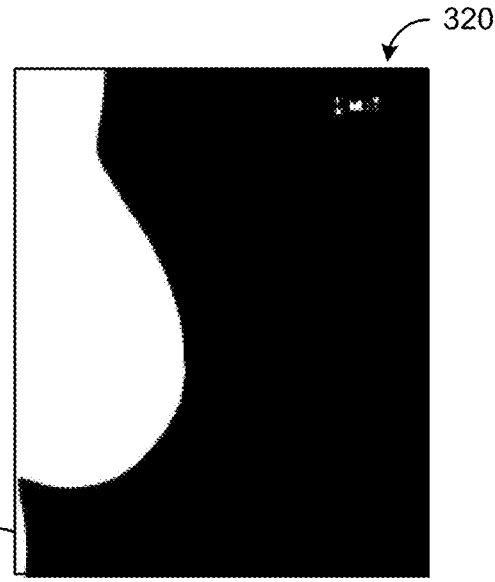
FIG. 3C is an example of a breast signal mask with the exterior part of the nipple removed.

For example, in at least one embodiment, the ROI generation module 226 may be configured to remove all or part of the nipple by locating two pairs of coordinates around the nipple, one on each side, and using these reference points to draw a geometric region, such as rectangle or arc, to remove from the breast signal mask. FIG. 3C illustrates a breast signal mask 320 with the exterior part of the nipple removed.

The ROI generation module 226 may be further configured to process the breast signal mask 320 to remove the region under the main breast. In the MLO view, this region is the chest wall, such as chest wall 325 illustrated in FIG. 3C. In the CC view, this region is the adjacent breast.

In at least one embodiment, the ROI generation module 226 may be configured to identify the region under the main breast region for removal by interrogating the gradient angles for the breast signal mask and identifying the gradient angle values likely to be the chest wall or adjacent breast. Based on the direction in which the breast in the pre-ROI image is facing, the ROI generation module 226 may search for gradient values, such as, for example, from 0 to 20 degrees and 340 to 360 degrees, or from 170 to 190 degrees, where the degrees are an indication of the orientation of the normal vectors between the dark areas (background) and light areas (breast signal mask). The gradient values may be calculated by applying filters, such as, but not limited to, a Sobel filter, for example, by applying the filter in both the x- and y-directions and converting the resultant Cartesian representation of the gradient to polar coordinates.

The search region within which the gradient values that are likely to be the chest wall may be defined by the size of the pre-ROI image and the likely placement of the nipple within the pre-ROI image, where the nipple location is available. This is because the chest wall is located below the nipple, and generally appears close to either the extreme right or extreme left of a mammogram image. Where the nipple location is not available, the location of the widest part of the breast is used.

Alternatively, in at least one embodiment, the ROI generation module 226 may be configured to remove the chest wall or adjacent breast by identifying a block based on two points creating an x,y coordinate of the corner of the ROI. The first point, identifying the y-coordinate ($y_1$) of the block, is a point identifying the top of the edges, selecting the point closest to the nipple or closest to ⅓ of the height of the image if the nipple could not be found. The top of the edges are identified through the gradient direction (as explained above). The second point, identifying the x-coordinate ($x_1$) of the block, is the point on the edge furthest from the left or right edge of the image, where the determination of the left or right edge depends on the laterality of the mammogram. The ROI generation module 226 may place zeros within this block defined by this $x_1,y_1$ point and the appropriate corner of the image and extract the largest remaining binary region as the refined breast signal mask.

Figure 3D:
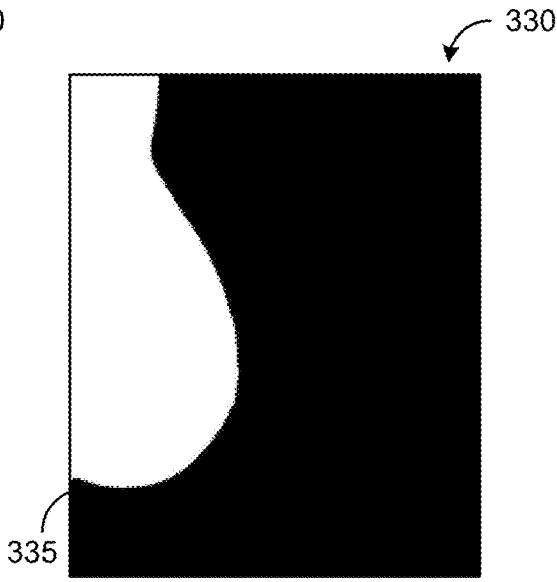
FIG. 3D is an example of a breast signal mask with the chest wall under the breast removed.

For an image illustrating a breast facing right on the image, the block may have as its coordinates (0, last column of image) and ($x_1,y_1$). For an image illustrating a breast facing left on the image, the block may have as its coordinates ($x_1,y_1$) and (last row of image, last column of image). FIG. 3D illustrates an example of an MLO view of a breast signal mask 330 with the chest wall 335 under the breast removed.

Figure 3E:
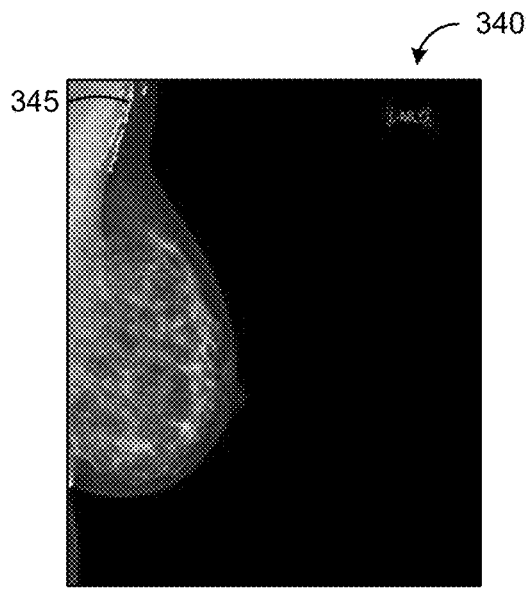
FIG. 3E is an example of detected regions, from a mammogram image, which contain the boundary between the breast tissue and the pectoralis muscles.

The ROI generation module 226 may also be configured to process the resultant breast signal mask to remove or suppress the pectoral muscles where it is present in a significant portion of the image. This occurs more often in the MLO view than the CC view image. FIG. 3E illustrates a boundary 345 between the breast tissue and the pectoral muscles in a breast image 340. In accordance with the teachings herein, it has been found that if the presence of the pectoral muscles within the mammogram is significant, it tends to interfere with the accurate detection of breast density.

Accordingly, in at least some embodiments, the ROI generation module 226 may be configured to remove the pectoralis muscles by using an appropriate method, such as, but not limited to the Hough transform, for example. The Hough transform approximates the pectoral muscles by a line. The ROI generation module 226 may generate a best-fitted line, using the Hough transform, for the majority of the detected pixels that are on the boundary of pectoralis muscle and breast tissue. The pectoralis muscle is removed based on the fitted line. FIG. 3E illustrates the detected pixels on the boundary between the pectoral muscles and the rest of the breast.

In at least some embodiments, the ROI generation module 226 may generate the best fitted Hough line by performing the following steps:

1. setting search boundaries based on breast signal mask parameters such as, but not limited to, image size and expected location of breast signal, for example;
2. finding the breast signal mask boundary edges as well as the minimum and maximum width of the breast signal mask;
3. identifying the region most likely to be on the pectoral muscles edge line; and
4. identifying the best fit line to the identified region most likely to be on the pectoral muscles edge line using Hough transformation.

Figure 3G:
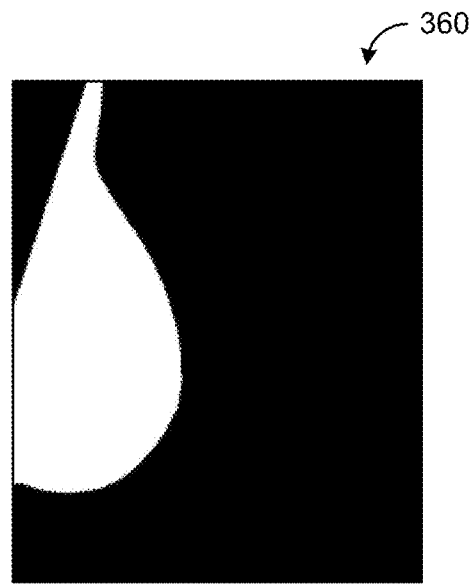
FIG. 3G is an example of a breast signal mask with the pectoral muscles, chest wall and nipple removed.
Figure 3F:
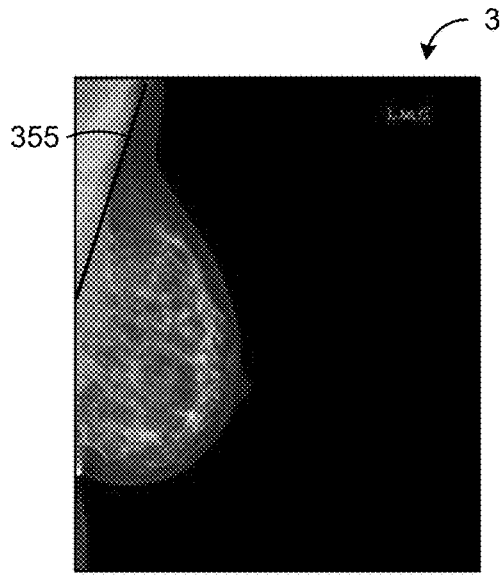
FIG. 3F is an example of a mammogram image illustrating a best fit line to the anterior portion of the pectoral muscles of FIG. 3C based on a Hough transform.

The Hough transformation may be carried out by using restrictions on the angular range of the fitted line and a minimum requirement for the number of pixels that contribute to the line. The restrictions may be dependent upon the orientation of the breast in the image and the resolution and size of the image. For example, the angular range may be defined from about pi/32 to about pi*15/64 radians for the left side MLO view and from about pi*13/16 to about pi*31/32 radians for the right side MLO view. The minimum requirement for the number of pixels may be described as being at least about 50. The ROI generation module 226 may then refine the breast signal mask based on the fitted line as generated. FIG. 3F illustrates a breast image 350 with the best fit line 355 to the pectoralis muscle based on the Hough transform. FIG. 3G illustrates a breast signal mask 360 with the pectoralis muscle removed.

Figure 3H:
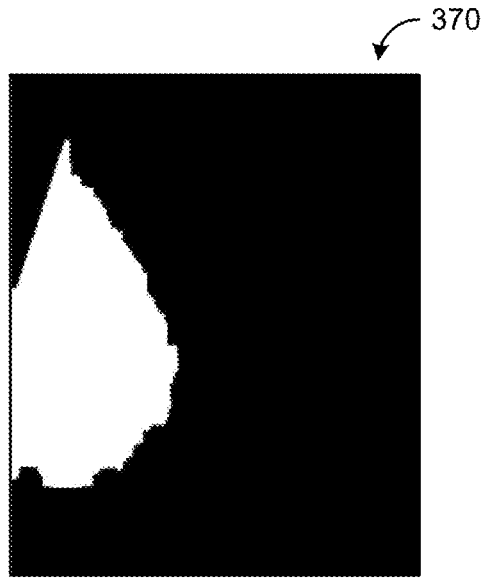
FIG. 3H is an example of a breast signal mask with the pectoral muscles, the nipple, and the subcutaneous fat removed.

The ROI generation module 226 may process a breast image to remove the subcutaneous fat region from the breast signal mask. In at least one embodiment, the ROI generation module 226 may create a ring area within the breast signal mask to extract a region containing a sample of subcutaneous fat to determine its intensity. In some embodiments, the ROI generation module 226 may create a ring area by subtracting an eroded version of the breast signal mask from the version of the breast signal mask immediately before the erosion process. The ROI generation module 226 may determine the maximum intensity within a portion of the ring area located between the nipple to the top of the breast signal mask. The ROI generation module 226 may then create a histogram of the intensities for the top part of the ring area, determine the mode of the histogram and set a subcutaneous fat threshold to this value multiplied by a constant. The ROI generation module 226 may then remove the subcutaneous fat by applying the subcutaneous fat threshold to the breast signal mask. FIG. 3H illustrates an example of a breast image 370 with the subcutaneous fat removed.

Figure 3I:
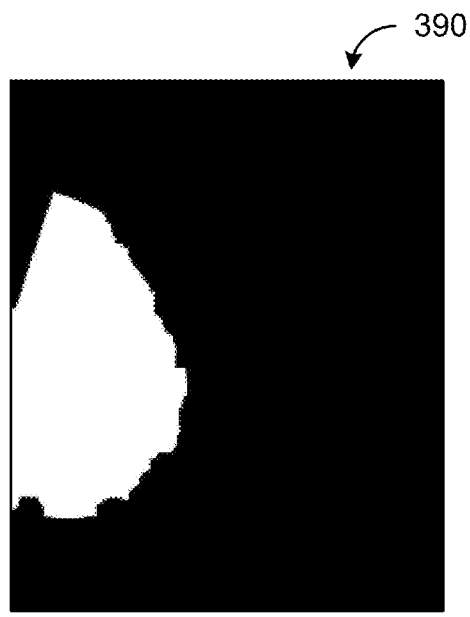
FIG. 3I is an example of a breast signal mask with the area in front of the pectoral muscles removed.

In some embodiments, the ROI generation module 226 may be configured to process the MLO view breast signal mask 370 to remove the region at the top of the breast in front of the pectoral muscles near the shoulder such that there is a minimal removal of breast signal. FIG. 3I illustrates an example of a breast mage 390 with the area in front of the pectoral muscles removed.

The ROI generation module 226 may remove this region by using an arc to alter the extent of the breast signal mask at the top of the image. In such embodiments, the size and placement of the arc is dictated by the centroid of the mask and the curvature of the breast signal mask in front of the pectoralis muscles with the subtending angle being defined so that only the top portion of the mask is affected.

In some embodiments, the ROI generation module 226 may be configured to process the MLO view breast signal mask 530 to remove skin fold regions if and when these regions are detected. The ROI generation module 226 may, in some embodiments, remove the skin fold regions by identifying regions at the bottom of the mask near the inframammary fold and regions at the top of the mask near the armpit. If edges indicative of folds are found, then the regions are removed. In some embodiments, the regions may be identified using an arc sector drawn such that it is centered at the horizontal image boundary ("x-coordinate") and such that the y-coordinate is dependent on a center of mass of the breast signal mask. The parameters used to draw the arc sector may be derived from the image signal content or image size. The ROI generation module 226 may search for edges in this arc sector using edge detection algorithms such as, but not limited to, for example, the Canny edge detector that requires the setting of the lower and upper hysteresis thresholds. The ROI generation module 226 may also require the edges to be of sufficient length. For example, if the arc sector is drawn near the armpit (top of image), the ROI generation module 226 may use 40 as the lower hysteresis threshold, 80 as the upper hysteresis threshold and may require the identifiable edge to contain at least 45 pixels.

In some embodiments, the ROI generation module 226 may be configured to fill holes, smooth boundaries and other methods of altering binary objects that are known to those skilled in the art.

Figure 3J:
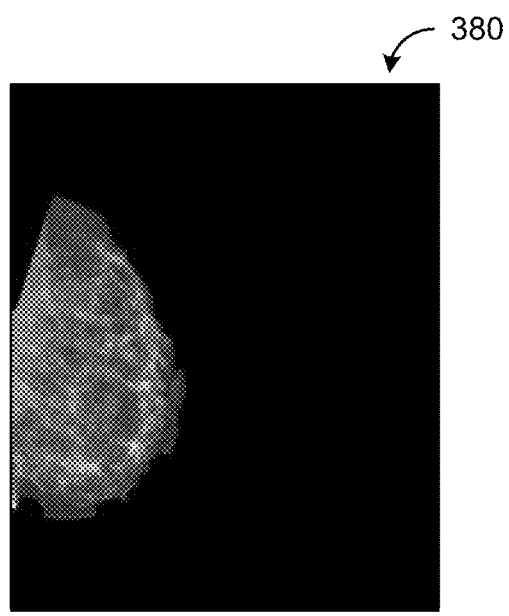
FIG. 3J is an example of a modified mammogram image containing only regions within the refined breast signal mask area.

FIG. 3J illustrates an ROI image 380 representing a breast tissue area generated after masking a pre-ROI image with a breast signal mask. The ROI generation module 226 determines the region of interest by generating an initial breast signal mask of the pre-ROI image and then refining the mask. The breast signal mask may be refined by carrying out some combination of the image processing steps just described herein for the ROI generation module 228 or all of the image processing steps just described herein for the ROI generation module 228. Refining the breast signal mask by carrying out all of the image processing steps may result in a higher accuracy as compared to carrying out only some of the steps.

For example, in some embodiments, refining the breast signal mask may only include removing the pectoral muscles. In some other embodiments, refining the breast signal mask may additionally or alternatively include removing the chest wall or adjacent breast under the breast. In some further embodiments, refining the breast signal mask may additionally or alternatively include removing the subcutaneous fat. In yet some further embodiments, refining the breast signal mask may additionally or alternatively include removing all or part of the nipple. In yet some further embodiments, refining the breast signal mask may additionally or alternatively include removing the portion of the region in front of the pectoral muscles near the shoulder.

Although FIGS. 3A-3J are illustrated herein using the MLO view of the digital mammograms, it should be understood that these concepts may be easily translated to the CC, ML, LM and other mammogram views.

The ROI image generated according to the various embodiments disclosed herein comprises a plurality of pixels with either zero or non-zero values. The non-zero values of the ROI image correspond to regions of intermediate image suitable for performing calculations upon.

The breast density measurement module 228 may interact with at least one of the memory unit 218 and the databases 230 to generate a breast density measurement corresponding to the input image. The breast density measurement module 228 may generate measurements for certain predictor variables from the region of the intermediate image, generated by the ROI generation module 226, where the region is defined by non-zero values of the ROI image. The breast density measurement module 228 then calculates the breast density value based on these measurements. Predictor variables are parameters that carry breast density signal information.

In some embodiments, the breast density measurement module 228 may output the breast density measurement as a percentage. In some other embodiments, the breast density measurement module 228 may output the breast density measurement as a number in a range of numbers. Other ways of outputting or reporting the breast density measurement may also be used.

The breast density measurement module 228 may generate measurements for predictor variables related to the histogram of the pixel intensity (e.g. histogram variables) and variables related to the texture of the image (e.g. texture variables). The measurements for the histogram and texture variables may be generated from the region in the intermediate image defined by the non-zero region of the ROI image, or from a sub-set of the non-zero region within the ROI image. In some embodiments, the measurements for the histogram and texture variables are generated from the intermediate image in a square region around a centroid of the ROI image.

Examples of histogram features may include, but are not limited to, at least one of skewness, entropy, maximum between class variance ninety nine percent index (i.e. the index of 99% area of the histogram) and fifty percent index (i.e. the index of 50% area of the histogram) etc. In some cases, the maximum between class variance is extracted by using automatic image threshold determination methods such as, but not limited to, the Otsu thresholding technique, for example.

Examples of texture features may include, but are not limited to, at least one of measures of the average gradient magnitude of the entire ROI image, measures of the average gradient magnitude of a portion of the ROI image, the edge ratio over the entire ROI image, and the edge ratio over a portion of the ROI image. The edges may be found through the use of the Canny edge detector or other edge detection algorithms.

The measurements for the histogram and texture variables obtained by the breast density measurement module 228 may be stored in memory, such as the memory 218 or the databases 230, in the corresponding image record.

Predictor variables also include some of the metadata information that was removed from the input image by the input module 224. In at least one embodiment, the predictor variables include a measure of laterality from the input image.

The breast density measurement module 228 calculates the breast density based on a breast density model that takes the form of a regression model that may be developed within statistical learning or machine learning frameworks. The breast density model is developed prior to everyday use of the breast density measurement system 200. The breast density model may be trained multiple times during the course of the use of the breast density measurement system 200, for example, due to various upgrades in manufacturer products that occur over time and may affect the quality of images that are used as the input image to the breast density measurement system 200.

The breast density model is trained using expert assessment of breast density on a set of training mammogram images. The training mammogram images may comprise 'for presentation' mammogram images, processed raw digital mammogram images, or both. The training of the breast density model may be performed using the features from 'for presentation' and/or processed raw digital mammogram images depending on the images to be processed by the final model.

The expert assessment of breast density may be used as a target to which the breast density model is trained. In at least one embodiment, the expert assessment may be based on the median of the percent density values from a panel of radiographers for a plurality of training digital mammogram images. The radiographers are trained mammographers who are considered experts in the field according to some accepted standard. These assessments from the radiographers may be visual assessments. These assessments from the radiographers may alternatively or additionally be pre-processed by an automated or semi-automated method. In some other cases, the assessments may be made using interval, ordinal, ordered nominal, unordered nominal or binary measurement scales. In some further cases, the measurement instrument may be a visual analog scale or a Likert scale, for example.

In order to perform this training, a modeling technique is selected for the breast density model. The modeling technique may be based on a predictive model in the field of statistics. In at least one embodiment, the particular structure is based on machine or statistical learning algorithms. Examples of machine learning or statistical learning algorithms may include, but are not limited to, supervised learning, unsupervised learning and semi-supervised learning, for example. Learning algorithms may include, but are not limited to, linear regression, multivariate adaptive regression splines (MARS), artificial neural network, classification and regression trees (CART), support vector machines, random forests, and ensemble learning algorithms (i.e. bagging and AdaBoost), for example.

In order to develop the model, a particular subset of predictor variables from the universe of potential predictor variables is selected such that when measurements for the selected predictor variables on a plurality of training digital mammogram images are provided as inputs to the breast density model, the resulting breast density values calculated by the breast density model are substantially similar or result in an acceptable approximation to the breast density values obtained by expert assessment. It should be noted that this training may be repeated for different subsets of predictor variables until a final set of predictor variables are determined that result in an acceptable level of performance compared to the expert assessments when used with the particular structure that was used for the breast density model. Alternatively, the structure for the breast density model, or different values for the parameters used in the breast density model, may also be varied and tested across the plurality of test images (images separate from those images used to develop the model) in order to determine a particular structure, or parameters for a particular structure, that result in an acceptable level of performance compared to the expert assessments when used with a final set of predictor variables.

The subset of predictor variables which result in an acceptable level of performance when used with a selected breast density model can be determined based on various techniques such as, but not limited to, feature selection, feature extraction and the like, for example. For example, in pattern recognition and image processing, feature extraction is a process by which new features (variables) are created from functions of the original features. In machine learning and statistics, feature selection is also known as variable selection, attribute selection or variable subset selection. Feature selection is the process of selecting a subset of relevant features from a larger set of possible features considered for use in model construction. Variable selection techniques may include the use of ensemble methods (also known in machine learning as committee methods or model combiners) such as, but not limited to, bagging (including, but not limited to, random forest, for example), boosting (including, but not limited to, boosted trees, for example), bucket of models, stacking, and the like. Some of the final predictor variables may also be selected based on the knowledge of those skilled in image processing in terms of which predictor variables may provide a useful amount of information or signal based on the physiological attributes of the breast, and breast density.

In at least some example embodiments described herein, the final set of predictor variables may include twelve (12) predictor variables, of which three (3) variables are based on the DICOM header information of a 'for presentation' or processed raw digital mammogram image, five (5) variables are based on histogram features of the ROI image for and four (4) variables are based on texture features of the ROI image.

In some embodiments, the variables removed from the DICOM header may include relative x-ray exposure, exposure duration and peak kilo-voltage; the variables corresponding to the histogram features may include skewness, entropy, maximum between class variance, ninety nine percent index and fifty percent index; and the variables corresponding to the texture features may include the average gradient magnitude of the region of the intermediate image identified by the non-zero region of the ROI image, the average gradient magnitude of the intermediate image identified by a portion or sub-set of the non-zero region of the ROI image, the edge ratio over the region of the intermediate image identified by the non-zero region of the ROI image, the edge ratio of the intermediate image identified by a portion or sub-set of the non-zero region of the ROI image, for example. It should be noted that in other embodiments, other combinations of predictor variables may be used which may provide better performance.

The breast density measurement module 228 applies the breast density model to new data in order to generate predictions or estimates of breast density. The estimated value of breast density for a particular digital mammogram is computed by the breast density measurement module 228 based on the measurements of the final set of predictor variables discussed herein that are used as inputs to the breast density model.

It should be noted that in alternative embodiments, the modules 224, 226 and 228 may be combined or may be separated into further modules. Furthermore, the modules 224, 226 and 228 are typically implemented using software, but there may be embodiments in which they may be implemented using FPGA, GPU, application specific circuitry or some other suitable technique.

The databases 230 can be used to store data for the system 200 such as system settings, parameter values and patient information for reporting purposes. The databases 230 can also store other information required for the operation of the programs 222 or the operating system 220 such as dynamically linked libraries and the like.

The operator unit 202 comprises at least one interface that the processing unit 204 communicates with in order to receive or send information. This interface can be the user interface 208, the interface unit 210 or the wireless unit 214. For instance, information for selecting certain predictor variables or using certain parameter values for the various image processing techniques used by the system 200 may be inputted by someone through the user interface 208 or it can be received through the interface unit 210 from another computing device. The processing unit 204 can communicate with either one of these interfaces as well as the display 206 or the I/O hardware 212 in order to output information related to the breast density measurement such as, but not limited to, the calculated breast density measurement value, any intermediate images or the values of certain predictor variables, for example. In addition, users of the operator unit 202 can use the interface unit 210 to communicate information across a network connection to a remote system for storage and/or further analysis. This communication can also include, but is not limited to, email communication, for example.

The user can also use the operator unit 202 to input information that is needed for system parameters that are needed for proper operation of the system 200 such as various parameter values and other system operating parameters as is known by those skilled in the art. Data that is obtained from the breast density calculation method, as well as parameters used for operation of the system 200, may be stored in the memory unit 218. The stored data may include one or more of input images, intermediate images, pre-ROI images and ROI images at various processing stages as well as other data as described herein.

Figure 4:
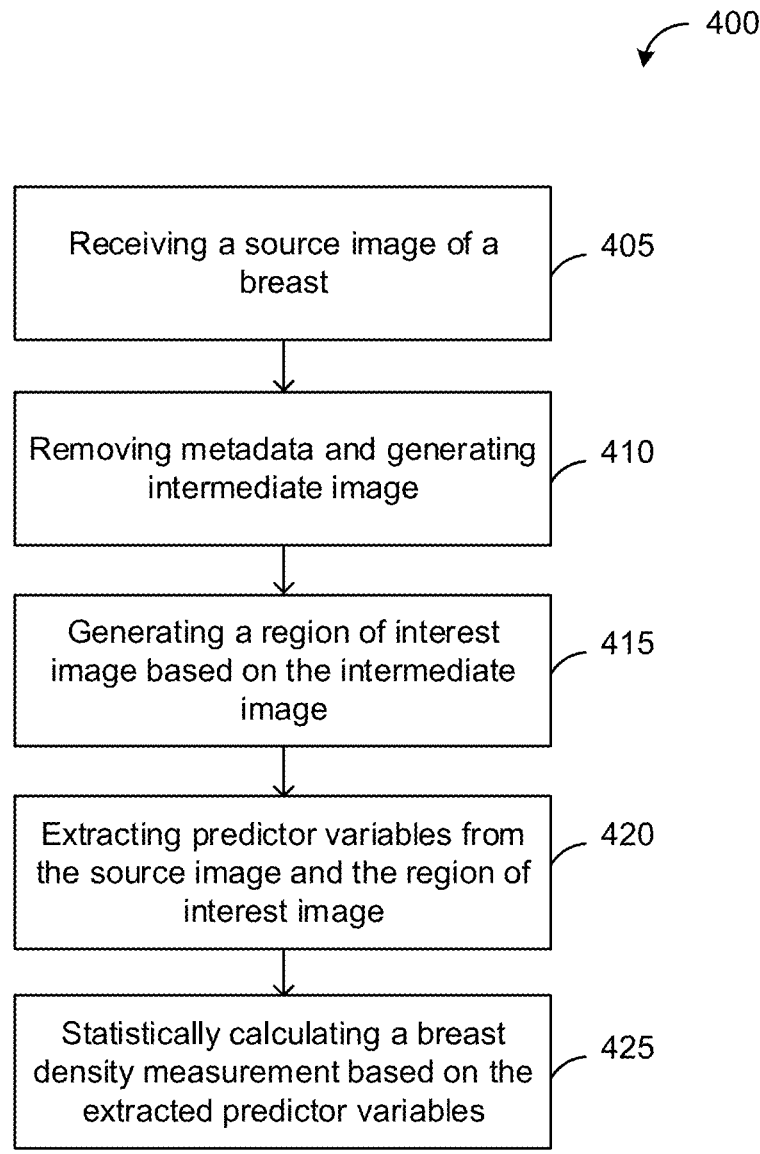
FIG. 4 is an example embodiment of a breast density determination method that may be used by a breast density measurement device or system.

Reference is next made to FIG. 4, illustrating an example embodiment of a breast density estimation method 400 in accordance with the teachings herein. The method 400 is carried out by the various modules of a breast density measurement system, such as the breast density measurement system 200.

At 405, an input image of a patient's breast is received. The input image may be a 'for presentation' or a processed raw digital mammogram image of the patient's breast. The 'for presentation' or processed raw digital mammogram image may be generated by using an x-ray imaging system made from a particular manufacture to expose the breast to x-rays, record an x-ray image and subject the x-ray image to post-processing methods (provided by the same or different manufacturer) to generate a digital mammogram that is suitable for viewing by radiologists.

In some cases, the input image is based on the DICOM (Digital Imaging and Communications in Medicine) standard, in which case the input image includes a DICOM header containing metadata information. In some other cases, the input image may alternatively be formatted according to some other standard.

In some further cases, the input image may not have a header containing metadata information. However, in such cases, the metadata information may be stored in a separate file or stored in a different manner, and the image information for the input image is stored in a certain image format such as, but not limited to, the TIFF (tagged image file format) format, for example. The header information and the image information can both be accessed by a breast density measurement system, such as the breast density measurement system 200.

At 410, metadata information is removed from the input image to generate an intermediate image. In most cases, the metadata information is removed from the header of the input image. In some other cases, the metadata information may be removed from other parts of the input image depending on how the image is formatted.

At 415, the intermediate image is processed to yield an ROI image. For example, the intermediate image may be processed to yield the ROI image as described with respect to FIG. 5 or FIG. 6.

At 420, measurements for predictor variables are generated from the intermediate image 410 and the ROI image as generated at 415. As previously explained, predictor variables are selected that generally provide an accurate calculation of the breast density from a 'for presentation' or processed raw digital mammogram image. Measurements for predictor variables based on the input image include metadata information. Measurements for predictor variables based on the ROI image comprise values for various histogram and texture features of the ROI image. Some histogram and texture features use the entire ROI image, while some others use a region within the ROI image. Examples of predictor variables were given in the description of the breast density measurement module 228 given previously.

At 425, the breast density is determined by applying the measurements of the predictor variables to the breast density model. As explained previously, the breast density model may be structured based on regression analysis modeling, machine learning or statistical learning algorithms, such as, but not limited to parametric, non-parametric and semi-parametric regression models, neural networks, and ensemble models.

Figure 5:
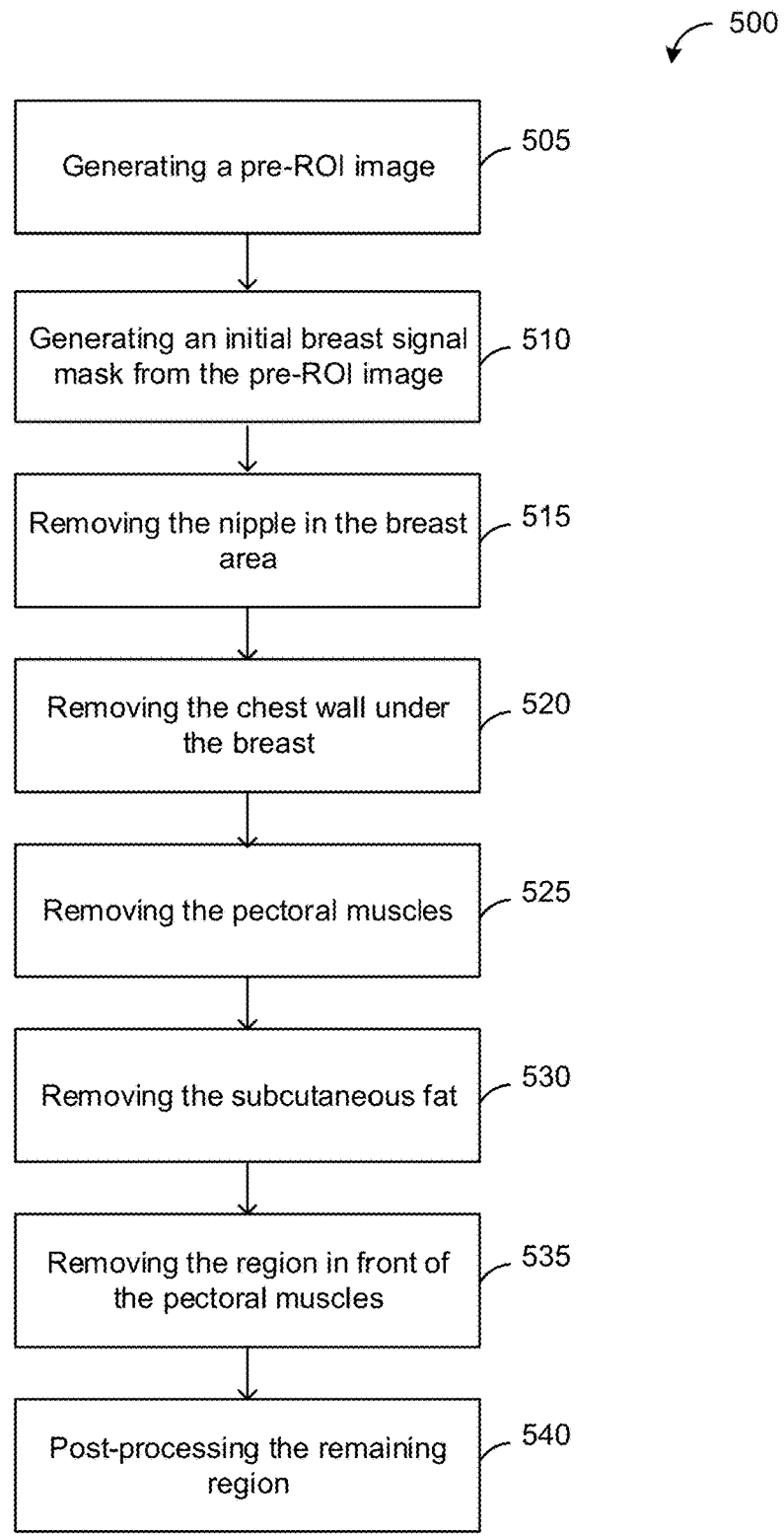
FIG. 5 is an example embodiment of a region of interest generation method that may be used by a breast density measurement device or system for MLO view images.

Reference is next made to FIG. 5, illustrating an example embodiment of an ROI image generation method 500 for MLO view images in accordance with the teachings herein. The method 500 may be carried out by various modules of a breast density measurement system, such as the breast density measurement system 200. For example, the method 500 may be carried out by an ROI generation module, such as the ROI generation module 226 of FIG. 2. The method 500 illustrates the processing of the intermediate image to generate the ROI image such that it represents the breast tissue of interest, which then allows for better performance of the breast density generation system and a more accurate breast density estimation to be made.

At 505, a pre-ROI image is generated based on the intermediate image. The pre-ROI image may be generated by processing the intermediate image to remove noise, unwanted signal and metadata, etc. from the intermediate image.

In some embodiments, the intermediate image is resized. The intermediate image may be resized by down sampling the intermediate image. For example, in at least one embodiment, the intermediate image may be resized to $1116^{th}$ of its original size. In some other embodiments, the intermediate image is resized by up sampling the intermediate image.

In some further embodiments, the resized image or the intermediate image is further processed to smooth the image. The resized image may be smoothed by using a smoothing filter such as, but not limited to, a Gaussian filter, a box filter, a low-pass filter, or anisotropic diffusion. Other algorithms may also be used to smooth the resized image.

In yet some further embodiments, the resized image, the smoothed image or the intermediate image is further processed to remove salt and pepper noise from the image. The de-noising may be carried out by applying linear or non-linear filters such as, but not limited to, a Rank detection filter (for example, a median filter), anisotropic diffusion, or exponential filter, for example.

In some other embodiments, the pre-ROI image is the same as the intermediate image. In such embodiments, no processing of the intermediate image is carried out.

At 510, an initial breast signal mask of the pre-ROI image is generated. The initial breast signal mask may be generated by separating the background of the pre-ROI image from the area containing the breast tissue.

At 515, the initial breast signal mask may be refined to remove the nipple in the breast area. The nipple is removed by using image processing algorithms. For example, the nipple may be removed by approximating the nipple area in the image, locating two pairs of coordinates around the nipple, drawing a line between the two points and removing the portion of the nipple using the line. Another example includes removing the interior of the nipple by drawing a geometric shape, such as rectangle or arc that extends further into the interior of the breast signal mask.

At 520, the region under the main breast, such as the chest wall in the MLO view, may be removed from the breast signal mask by applying further image processing which may be done as described herein with respect to the ROI generation module 226. Alternatively, other techniques may be used as is known to those skilled in the art.

At 525, the breast signal mask may be further refined to remove the pectoral muscles. The pectoral muscles may be removed by using image processing algorithms such as, but not limited to, using the Hough transformation to model the boundary of the pectoralis muscle and the breast, for example.

At 530, the breast signal mask may be further processed to remove the subcutaneous fat which may be done as described herein with respect to the ROI generation module 226. Alternatively, other techniques may be used as is known to those skilled in the art.

At 535, the breast signal may be further processed to remove the region at the top of the breast in front of the pectoral muscles near the shoulder. This region may be removed as described herein with respect to the ROI generation module 226. Alternatively, other techniques may be used as is known to those skilled in the art.

At 540, an ROI image is generated. Post-processing to smooth the boundaries, fill holes, and/or remove regions where skin folds are present may be employed. The ROI image represents the region of the breast that will be used to extract image-based features.

In some embodiments, the initial breast density mask may be refined to only remove the pectoral muscles, such as at step 525 in FIG. 5. In such embodiments, steps 515, 520, 530, 535 and 540 of FIG. 5 are optional. In some other embodiments, refining the breast signal mask may additionally include removing a region, such as the chest wall, under the main breast, such as at step 520 in FIG. 5. In such embodiments, method 500 may further include locating the nipple location or approximating the nipple area and removing the nipple in the image, as described above. In such embodiments, steps 525, 530, 535 and 540 of FIG. 5 are optional.

In some embodiments, method 500 may include refining the breast signal mask by removing the pectoral muscles and subcutaneous fat, such as at steps 525 and 530 in FIG. 5, respectively. In such embodiments, method 500 may further include locating and removing all or part of the nipple in the image, as described above. In such embodiments, steps 520, 535 and 540 of FIG. 5 are optional.

In some other embodiments, method 500 may include refining the breast signal mask by removing some or all part of the nipple in the breast area, such as at step 515, and removing the pectoral muscles, such as at step 525 in FIG. 5, respectively. In such embodiments, steps 520, 530, 535 and 540 of FIG. 5 are optional.

In another embodiment, refining the breast signal mask may include removing the pectoral muscles, such as at step 525 and removing a portion of the region in front of the pectoral muscles near the shoulder, such as at step 535 in FIG. 5. In such embodiments, steps 515, 520, 530 and 540 are optional.

In some further embodiments, method 500 does not include any processing steps 515 to 540. In such embodiments, the ROI image is generated based on the initial breast signal mask generated at step 510 of FIG. 5. This embodiment may result in a less accurate breast density measure since it involves rough approximation of the breast tissue region within the pre-ROI image.

It should be noted that in other embodiments there may be other combinations of steps 515 to 540 that may be carried out by the breast density measurement system to generate an ROI image.

Figure 6:
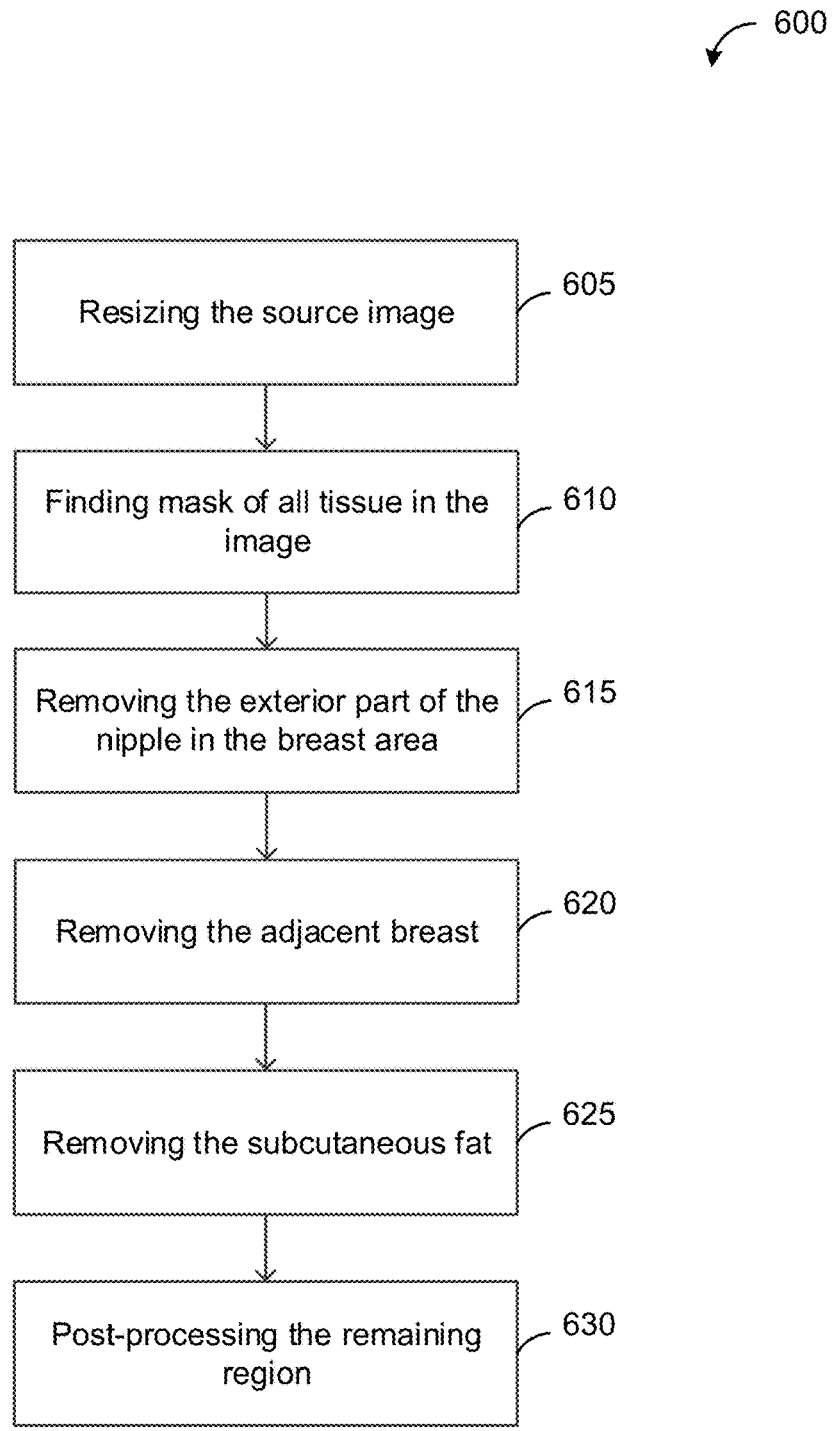
FIG. 6 is an example embodiment of a region of interest generation method that may be used by a breast density measurement device or system for CC view images.

Reference is next made to FIG. 6, which illustrates an example embodiment of an ROI image generation method 600 for CC view images in accordance with the teachings herein. The method 600 may be carried out by various modules such as, for example, those that are included in the breast density measurement system 200. For example, the method 600 may be carried out by an ROI generation module, such as the ROI generation module 226 of FIG. 2. The method 600 illustrates the processing of an intermediate image to generate the ROI image such that it represents the breast tissue of interest, which then allows for better performance of the breast density generation system and a more accurate breast density calculation to be made.

Steps 605, 610, 615, 625 and 630 of FIG. 6 generally correspond to steps 505, 510, 515, 530 and 540 of FIG. 5 respectively. At 620 of FIG. 6, the adjacent breast is removed from the breast signal mask by applying further image processing as discussed above. Unlike the MLO view, the CC view does not typically show the pectoral muscles. Therefore, the step of removing the pectoral muscles, such as in step 535 of FIG. 5, may not be required in the processing of CC view image to generate an ROI image.

Figure 7A:
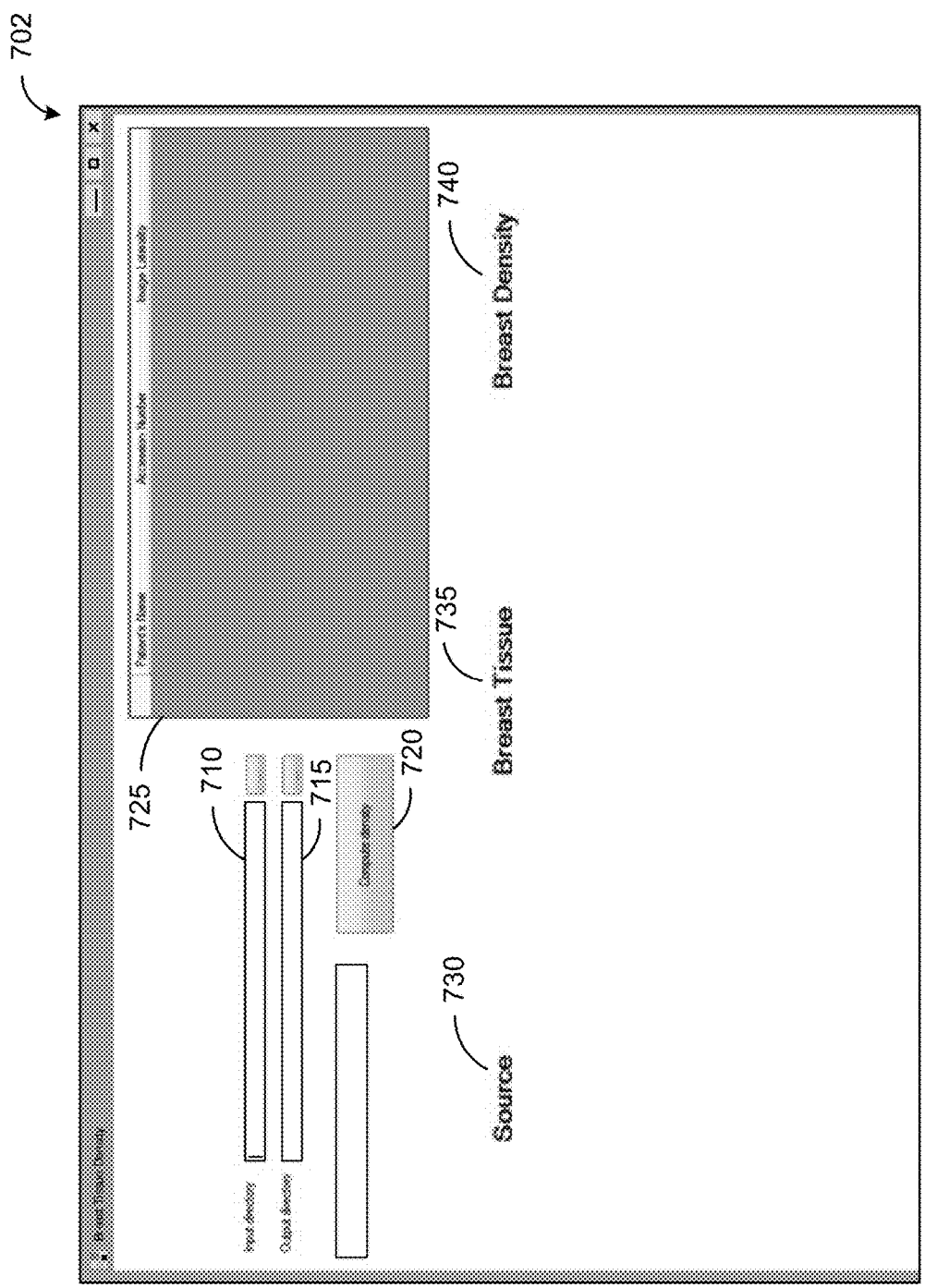
FIG. 7A illustrates a user interface for breast density measurement system according to one example embodiment.
Figure 7B:
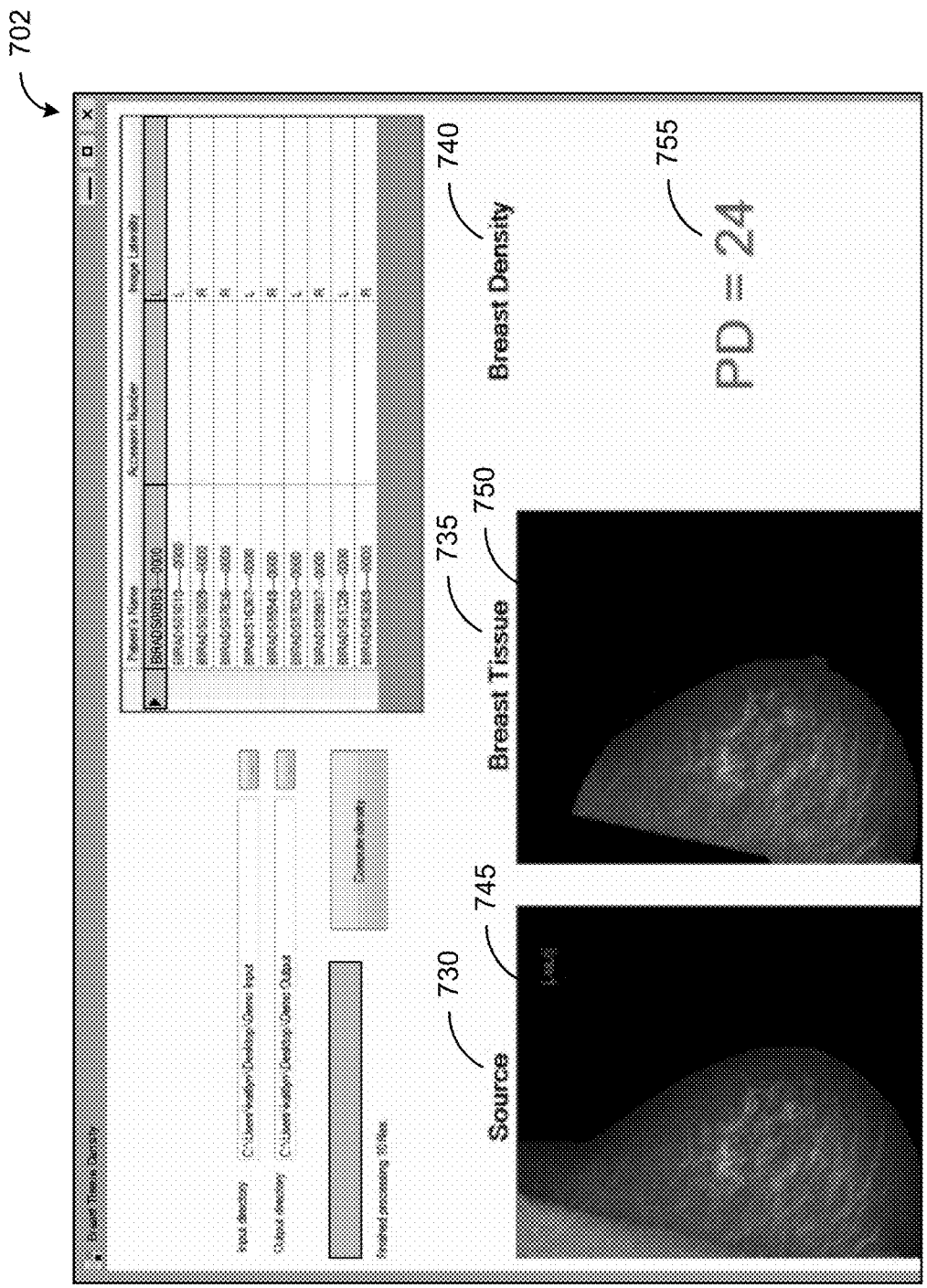
FIG. 7B illustrates a user interface for breast density measurement system according to another example embodiment.

Reference is next made to FIGS. 7A-7B, which illustrate screenshots of an example embodiment of a user interface (UI) 702 that may be used with a breast density measurement system, such as in the user interface 208 of operator unit 202 of breast density measurement system 200. The UI 702 illustrates an input file selection tab 710, an output file selection tab 715, compute density tab 720, image record table 725, source label 730, breast tissue label 735 and breast density label 740.

The input file selection tab 710 allows the user of the breast density measurement system, such as a radiologist, to access a database of input files containing digital mammogram images. The input file selection tab 710 further allows the user of the breast density measurement system to select a desired input file from the database of input files.

Each input file may contain one or more digital mammogram images of one or more patients. In some cases, each input file contains patient specific digital mammogram images that are obtained over the duration of some treatment or in population screening. In some other cases, each input file contains digital mammogram images for patients assessed by radiologists on the same day. Each input file may contain a plurality of digital mammogram images according to some other criteria.

In addition to digital mammogram images, each input file may further include additional information related to the digital mammogram images. Such additional information may include identification information such as, but not limited to, one or more of a patient's name or patient identifier, an exam name or exam identifier, an image laterality, an image view (e.g. MLO or CC), and other related information. This information may be displayed in the user interface for the radiologist's convenience.

The output file selection tab 715 allows the user to provide a path to a directory or a folder where the output of the breast density measurement system is saved. As previously mentioned, the output of the breast density measurement system is a breast density value, which may be expressed as a percentage, a number within a range or any other suitable metric. In addition to saving the breast density value, additional entries such as measurements for predictor variables may also be saved in the output file. Each output file may contain breast density value and/or measurements for predictor variables for one or more patients.

The compute density tab 720, as illustrated, is a button which when clicked, triggers the breast density measurement system, such as the breast density measurement system 200, to begin processing the input file, such as that identified in the input file selection tab 710, to generate breast density values for corresponding digital mammogram images contained in the input file. In some embodiments, some or all of the mammogram images stored in the input file are processed in parallel upon clicking the computer density tab 720. In some other embodiments, some or all of the mammogram images stored in the input file are processed sequentially upon clicking the compute density tab 720.

The image record table 725 illustrates a list of digital mammogram images stored in the input file selected at the input file selection tab 710. In the illustrated embodiment, for each digital mammogram image, the image record table 725 identifies the patient's name, accession number and image laterality. In other embodiments, the image record table 725 may indicate other information corresponding to the digital mammogram images stored in the selected input files.

The source label 730 identifies a region in the user interface 702 where the digital mammogram image that is used as an input image by the breast density measurement system in determining breast density is displayed. As illustrated in FIG. 7B, the location where the source image 745 is displayed is identified by the source label 730.

The breast tissue label 735 identifies a region in the user interface 702 where a digital image of a breast tissue or a ROI resulting from processing of the source image by using various processes illustrated herein, such as processes illustrated in FIG. 5 and FIG. 6, is displayed. FIG. 7B, label 750 illustrates an intermediate image which has had all values outside of the region identified by the ROI image set to zero and whose location is identified by the breast tissue label 735.

The breast density label 740 identifies a region in the user interface 702 where the breast density value that was determined for the source image is displayed. As illustrated in FIG. 7B, the breast density value 755 is a number. In some other embodiments, the breast density value may be a percentage, or some other representation of breast density, such as, for example, a graph.

Reference is next made to FIGS. 8A-8D, which illustrate performance statistics of example embodiments of a breast density measurement system, such as breast density measurement system 200, illustrated herein. The performance of the breast density measurement system is measured by comparing the system's assessments to several radiologists' assessments. In the illustrated statistics, the performance of the breast density measurement system is measured using an Intraclass Correlation Coefficient. Such statistics and graphs such as, for example, scatter plots, are standard measures that may be used to assess algorithm performance.

Figure 8A:
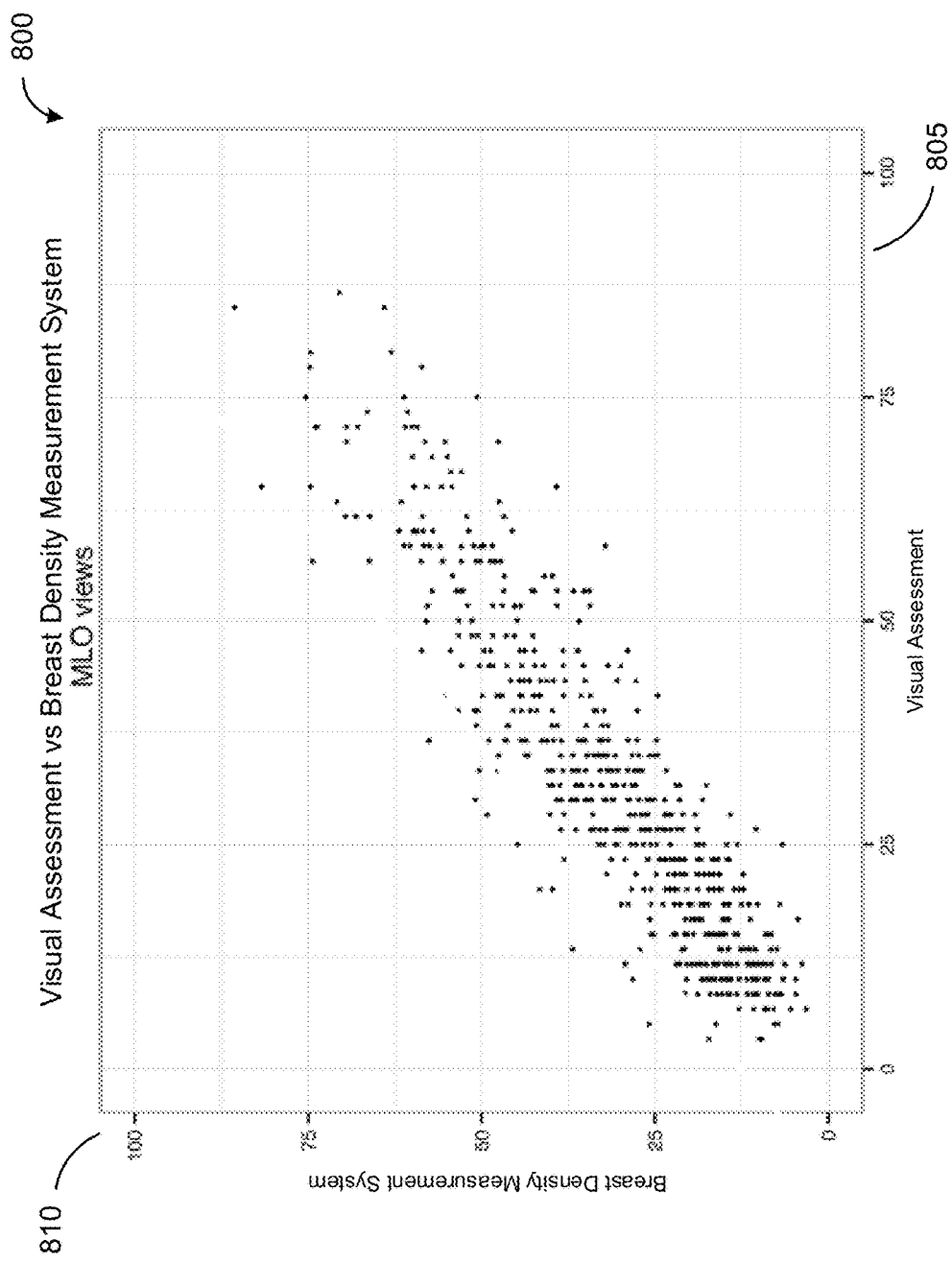
FIG. 8A illustrates a graphical representation of performance measure of breast density measurement system for MLO view digital mammogram images according to one example embodiment.

Reference is first made to FIG. 8A, which illustrates a graphical representation 800 of a performance measure of breast density measurement system for MLO view digital mammogram images. In this embodiment, the breast density measurement system utilizes the Support Vector Machine algorithm for the breast density model and is trained using the mean values of three radiologists' assessments on 1194 MLO view mammogram images. The trained breast density measurement system is then validated using the mean value of three radiologists' assessments on a separate set of 598 MLO view mammogram images.

As illustrated in FIG. 8A, the x-axis 805 corresponds to the mean breast density values from the assessments of three radiologists on 598 MLO view mammogram images. The y-axis 810 corresponds to the breast density values determined by this example embodiment of the breast density measurement system on the same 598 images. As illustrated in graph 800 of FIG. 8A, the agreement between the algorithm and the mean radiologist assessment is excellent as shown by the Intraclass Correlation Coefficient which is 0.899 (95% confidence intervals 0.882 to 0.913).

Figure 8B:
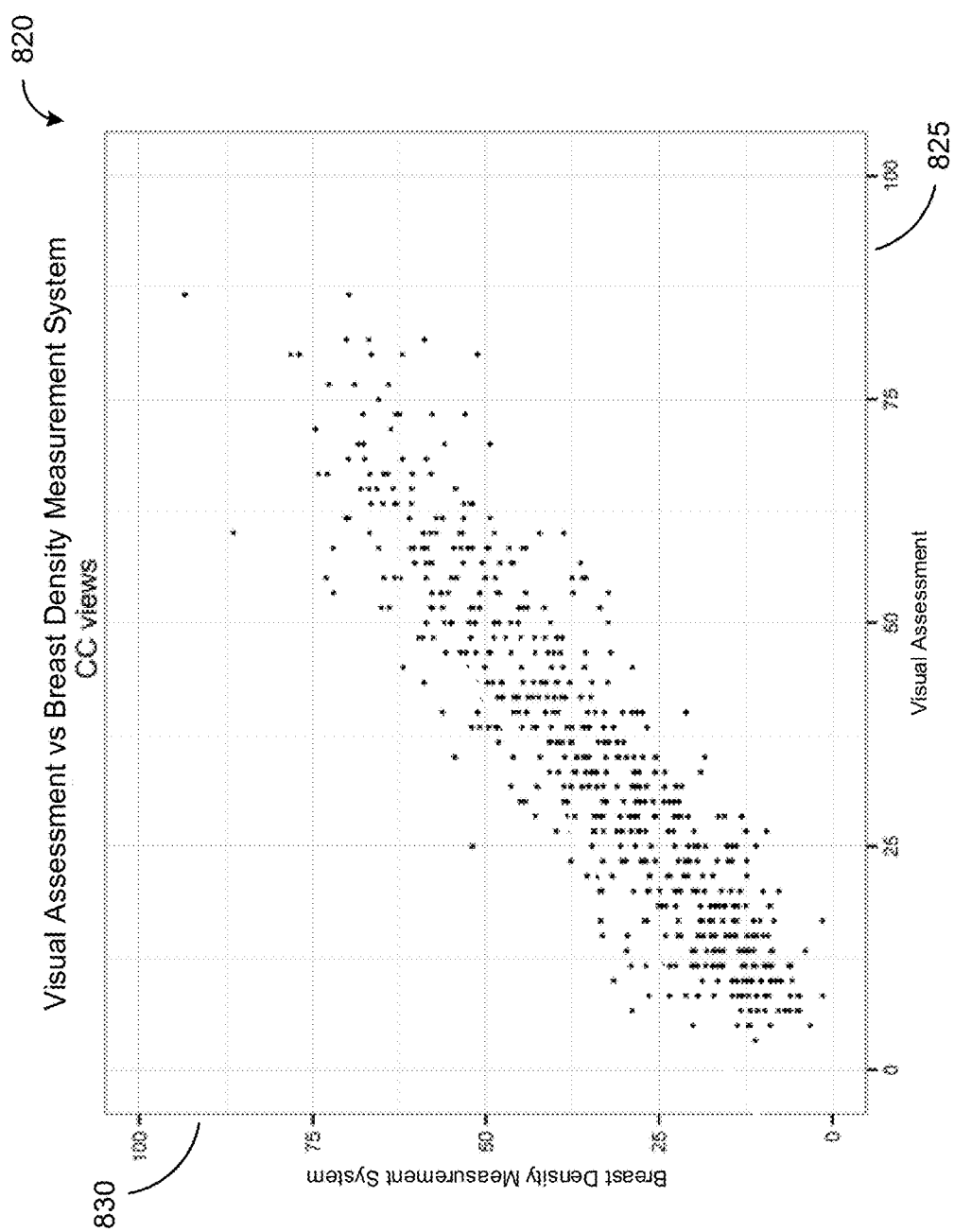
FIG. 8B illustrates a graphical representation of performance measure of breast density measurement system for CC view digital mammogram images according to one example embodiment.

Reference is next made to FIG. 8B, which illustrates a graphical representation 820 of a performance measure of an example embodiment of the breast density measurement system for CC view digital mammogram images. In this case, the breast density measurement system utilizes a Support Vector Machine algorithm for the breast density model and is trained using the mean value of three radiologists' assessments on 1194 CC view mammogram images. The breast density measurement system is validated using the mean value of three radiologists' assessments on a separate set of 598 CC view mammogram images.

As illustrated in FIG. 8B, the x-axis 825 corresponds to the mean breast density value from the assessment of three radiologists on 598 CC view mammogram images. The y-axis 830 corresponds to the breast density values calculated by the breast density measurement system on the same 598 images. As illustrated in graph 820 of FIG. 8B, the agreement between the algorithm and the mean radiologist assessment is excellent with an Intraclass Correlation Coefficient of 0.908 (95% confidence intervals 0.892 to 0.921).

Figure 8C:
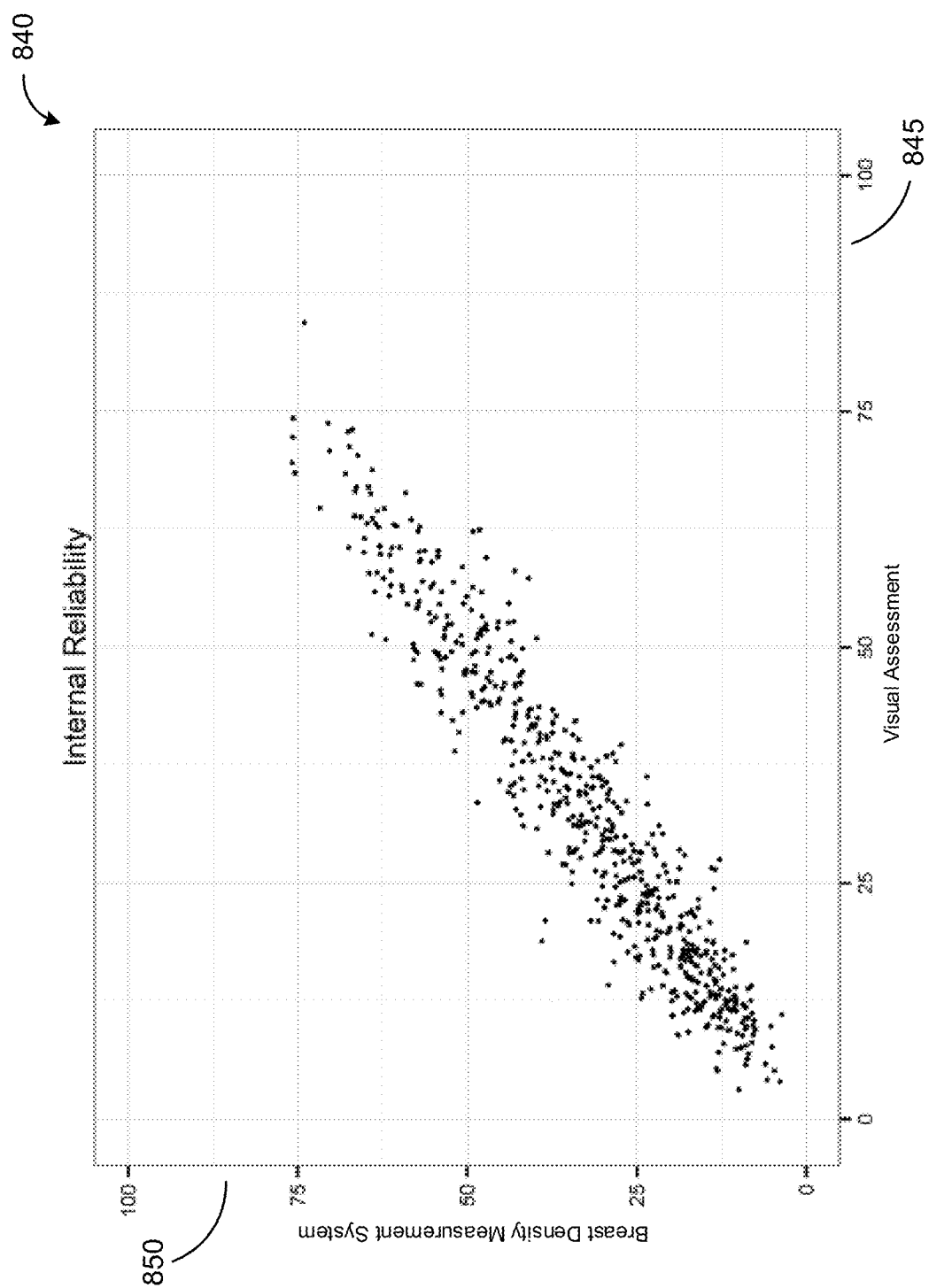
FIG. 8C illustrates a graphical representation of performance measure of breast density assessment system for left and right breast mammogram images according to one example embodiment.

Reference is next made to FIG. 8C, which illustrates a graphical representation 840 of a performance measure for a breast density assessment system on left and right breast mammogram images. In this case, the breast density measurement system utilizes a Support Vector Machine (SVM) algorithm for the breast density models and is trained using the mean value of three radiologists' assessments on 1194 CC view and 1194 MLO view mammogram images. The breast density measurement system is validated by using the mean of the left CC breast density and left MLO breast density, and the mean of the right CC breast density and right MLO breast density. In particular, the breast density measurement system is validated using a separate set (i.e. separate than the training images) of 598 mean breast densities of left CC and left MLO pairs and 598 mean breast densities from the corresponding right CC and right MLO pairs.

In this case, the x-axis 845 corresponds to breast density values for the right breast mammogram images of 598 subjects as determined by the breast density measurement system. In particular, the x-axis 845 corresponds to an average of breast density values as determined for MLO and CC views of the right breast mammogram images of 598 subjects.

The y-axis 850 corresponds to breast density values for corresponding left breast mammogram images of the same 598 subjects as determined by the same embodiment of the breast density measurement system. In particular, the y-axis 850 corresponds to an average of breast density values as determined for MLO and CC views of corresponding left breast mammogram images.

As illustrated in graph 840 of FIG. 8C, the left and right breast density values as calculated using the breast density measurement system in this example embodiment are highly correlated with Person's correlation coefficient, rho, of 0.95, and Intraclass correlation coefficient of 0.954 (95% Confidence intervals of 0.946 to 0.96).

Figure 8D:
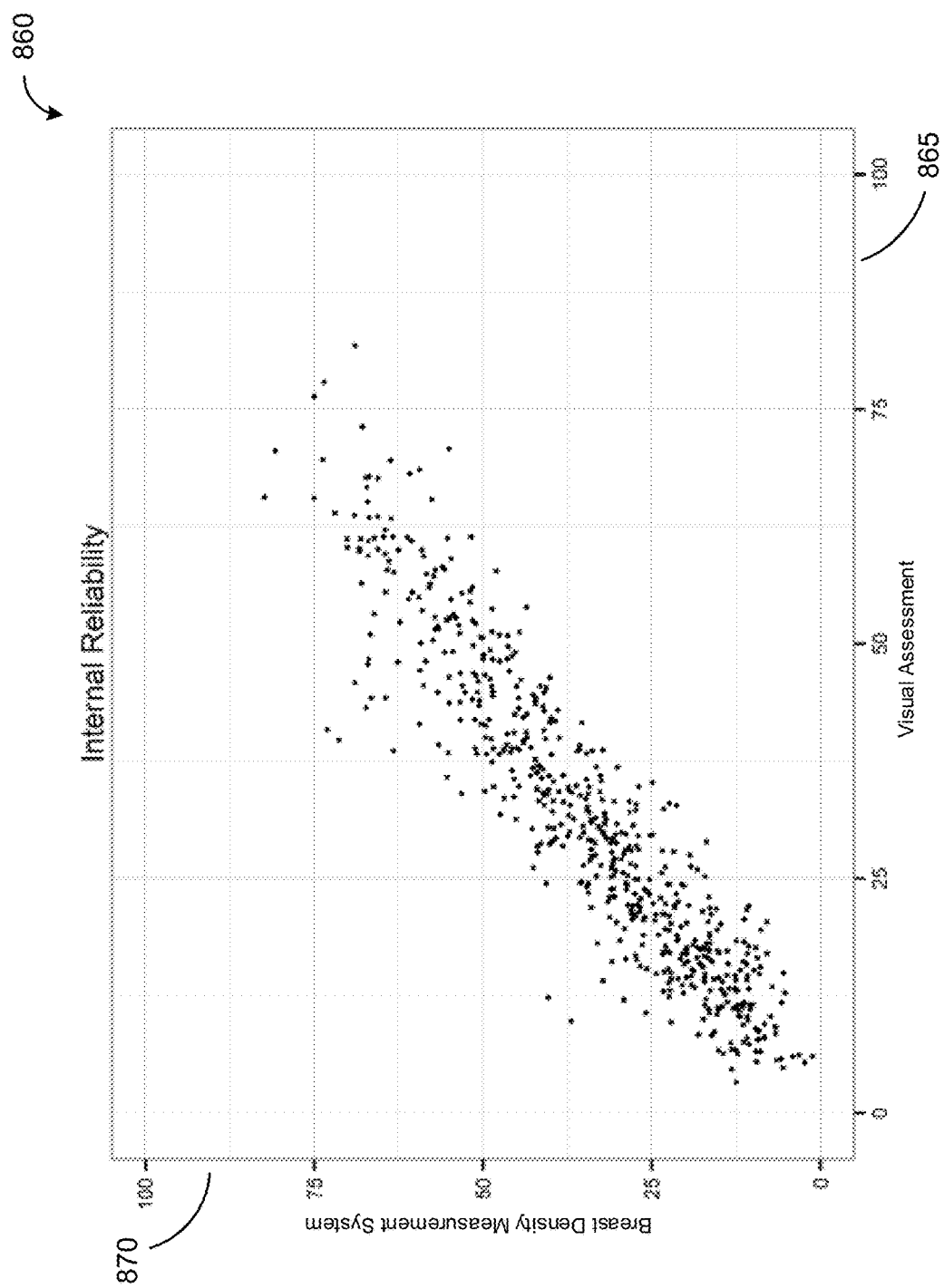
FIG. 8D illustrates a graphical representation of performance measure of breast density assessment system for CC and MLO views of left breast mammogram images according to one example embodiment.

Reference is now made to FIG. 8D, which illustrates a graphical representation 860 of a performance measure of an example embodiment of a breast density assessment system for CC and MLO views of left breast mammogram images. In this case, the x-axis 865 corresponds to breast density values calculated for MLO views of the left breast mammogram images of 598 subjects. The y-axis 870 corresponds to breast density values calculated for corresponding CC views of the left breast mammogram images of 598 subjects. As illustrated in graph 875 of FIG. 8D, the breast density values of the MLO and CC views of the left breast mammogram images are highly correlated with Person's correlation coefficient, rho, of 0.93, and an Intraclass correlation coefficient of 0.926 (95% Confidence intervals of 0.914 to 0.937).

The analysis illustrated in FIGS. 8A-8D were performed using the statistical software package "R" from the Comprehensive R Archive Network (CRAN). The version of R that was used was 3.0.1 (2013 May 16), and the platform used was x86_64-pc-linux-gnu (64-bit). R is an open source software environment for statistical computing and graphics and is widely used among statisticians and those skilled in the art.

In addition, the Intraclass Correlation Coefficient used in the analysis illustrated in FIGS. 8A-8D is from the 'irr' package v.0.84 (icc function). The parameters selected for this package include a "twoway" model, "consistency" type and "single" unit. The Pearson's correlation coefficients used in the analysis illustrated in FIGS. 8A-8D are from the Hmisc package v.3.14-4 (rcorr function). The parameter selected for this package includes "pearson" type.

In some embodiments, a breast density model according to the teachings herein may be embedded in an on-site server or computer that processes 'for presentation' or processed raw digital mammograms from a PACS device, an imager or other mammogram acquisition and storage devices. The on-site server or computer may be located within a hospital, clinic, personal setting or research setting, and is considered on-site if it is connected to a mammogram acquisition and storage device via LAN, VLAN, Bluetooth or wired connections. In such embodiments, the mammogram images may be provided to the breast density model through gestures, such as, drag and drop, cut and save, copy and save etc.

In some other embodiments, the breast density model according to the teachings herein may be embedded in a cloud-based server or other off-site server that processes 'for presentation' or processed raw digital mammograms from a PACS device, an imager or other mammogram acquisition and storage devices. In such embodiments, the mammogram acquisition and storage system may be located in a hospital, clinic, personal setting or research setting and the mammogram images may be provided to the off-site or cloud server via Internet. For example, in such embodiments, the mammogram images may be uploaded to the cloud server using web-browser interface from a mammography workstation device, and the results may be similarly downloaded from the cloud server.

In some embodiments, the breast density model according to the teachings herein and the mammogram acquisition and storage systems may be incorporated within a same system. In some other embodiments, the breast density model and the mammogram acquisition and storage systems may be implemented separately.

In various embodiments, the input images may be assessed for suitability (type, view, etc.) and placed in a queue until processing resources are available. After processing, the calculated values and identifiers may be logged within the system database. The resultant output data may then be sent to one or more input/output devices, such as the PACS, EMR, mammogram review stations, other HIT systems, personal computers and communication devices, etc., in appropriate format. The formats may include DICOM Structured Report (SR), DICOM Secondary Capture (SC), DICOM Greyscale Softcopy Presentation State (GSPS), HL7, xml format, standard computer formats such as portable document format (pdf) or comma separated values (csv), and other formats known to those skilled in the art. The reported values may display automatically at the input/output device or may require user initiation to view.

Various embodiments of systems, devices and methods that can be used to calculate breast density have been described here by way of example only. Various modifications and variations may be made to these example embodiments without departing from the spirit and scope of the embodiments, which is limited only by the appended claims which should be given the broadest interpretation consistent with the description as a whole.

We claim:

1. A system for determining a breast density value from a mammogram image of a breast, the system comprising:
   a memory unit;
   a processing unit that is coupled to the memory unit and controls operation of the system;
   an input module that interacts with the memory unit and is configured to receive an input image corresponding to the digital mammogram and remove metadata information from the input image to generate an intermediate image;
   a region of interest (ROI) generation module that is configured to generate an ROI image based on the intermediate image;
   a breast density model that is developed using a statistical learning algorithm, a machine learning algorithm or regression analysis modelling; and
   a breast density measurement module that is configured to extract values for predictor variables from the metadata information, the intermediate image and the ROI image; and calculate the breast density measurement by providing the values of the predictor variables as inputs to the breast density model.

2. The system of claim 1, wherein the breast density model is trained using measures of breast density values from expert assessment of breast density on a set of training mammogram images comprising at least one of processed raw digital mammogram images and 'for presentation' digital mammogram images that are raw digital mammogram images that have been enhanced for viewing by a human observer.

3. The system of claim 2, wherein the statistical learning algorithm or the machine learning algorithm include one of linear regression, parametric regression models, non-parametric regression models, semi-parametric regression models, multivariate adaptive regression splines, artificial neural networks, classification and regression trees, random forests, support vector machines, random forests, ensemble models and ensemble learning algorithms.

4. The system of claim 2, wherein the system further comprises a display that is coupled to the processing unit and is configured to display a user interface that shows the input image, the intermediate image and the breast density measurement.

5. The system of claim 2, the processing unit is configured to generate a report that contains the breast density measurement and has a format according to one of a DICOM Structured Report (SR), DICOM Secondary Capture (SC), or DICOM Greyscale Softcopy Presentation State (GSPS) and sends the report to one of a (Picture Archiving and Communication System) PACS, an Electronic Medical Record (EMR) system, a mammogram review station, a Hospital Information Technology (HIT) system, a personal computer, and communication devices.

6. The system of claim 2, wherein the intermediate image is processed to generate a pre-ROI image by removing noise from the intermediate image and the ROI image is generated by processing the pre-ROI image by optionally resizing the intermediate image.

7. The system of claim 2, wherein the metadata information that is removed from the input image comprises DICOM header information, and the predictor variables from the metadata information comprise at least one of patient specific parameters, image acquisition device parameters and image acquisition parameters.

8. The system of claim 7, wherein the image acquisition parameters comprise at least one of relative x-ray exposure, exposure duration, laterality, patient orientation and peak kilo-voltage;
the patient specific parameters comprise at least one of age of the patient, gender of the patient, patient date of birth, and patient identification information; and
the image acquisition device parameters comprise at least one of name and model of the device used to obtain the digital mammogram.

9. The system of claim 2, wherein the predictor variables comprise histogram features including at least one of skewness, entropy, maximum between class variance, ninety nine percent index and fifty percent index.

10. The system of claim 2, wherein the predictor variables comprise texture features including at least one of average gradient magnitude value of the intermediate image within the region defined by the non-zero values of the ROI image, an average gradient magnitude value of the intermediate image within a subset of the region defined by the non-zero values of the ROI image, an edge ratio of the intermediate image in the region defined by the non-zero values of ROI image, and an edge ratio of the intermediate image within a subset of the region defined by the non-zero values of ROI image.

11. A method of determining a breast density measurement from a digital mammogram, the method being performed by a processing unit, the method comprising:
receiving an input image corresponding to the digital mammogram;
removing metadata information from the input image to generate an intermediate image;
generating a region of interest (ROI) image based on the intermediate image;
extracting values for predictor variables from the metadata information, the intermediate image and the ROI image; and
calculating the breast density measurement based by providing the values of the predictor variables to a breast density model that is developed using a statistical learning algorithm, a machine learning algorithm or regression analysis modelling.

12. The method of claim 11, wherein the method comprises training the breast density model using measures of breast density values from expert assessment of breast density on a set of training mammogram images comprising at least one of processed raw digital mammogram images and 'for presentation' digital mammogram images that are a raw digital mammogram images that have been enhanced for viewing by a human observer.

13. The method of claim 12, wherein the statistical learning algorithm or the machine learning algorithm include one of linear regression, parametric regression models, non-parametric regression models, semi-parametric regression models, multivariate adaptive regression splines, artificial neural networks, classification and regression trees, random forests, support vector machines, random forests, ensemble models and ensemble learning algorithms.

14. The method of claim 12, wherein the method comprises displaying a user interface that shows the input image, the intermediate image and the breast density measurement.

15. The method of claim 12, wherein the method further comprises generating a report that contains the breast density measurement and has a format according to one of a DICOM Structured Report (SR), DICOM Secondary Capture (SC), or DICOM Greyscale Softcopy Presentation State (GSPS) and sending the report to one of a (Picture Archiving and Communication System) PACS, an Electronic Medical Record (EMR) system, a mammogram review station, a Hospital Information Technology (HIT) system, a personal computer, and communication devices.

16. The method of claim 12, wherein the method comprises processing the intermediate image to generate a pre-ROI image by removing noise from the intermediate image and the ROI image is generated by processing the pre-ROI image by optionally resizing the intermediate image.

17. The method of claim 12, wherein the method comprises removing DICOM header information from the input image and obtaining the values for the predictor variables from the metadata information from at least one of patient specific parameters, image acquisition device parameters and image acquisition parameters.

18. The method of claim 17, wherein the image acquisition parameters comprise at least one of relative x-ray exposure, exposure duration, laterality, patient orientation and peak kilo-voltage;
the patient specific parameters comprise at least one of age of the patient, gender of the patient, patient date of birth, and patient identification information; and
the image acquisition device parameters comprise at least one of name and model of the device used to obtain the digital mammogram.

19. The method of claim 12, wherein the method comprises obtaining the values for the predictor variables from histogram features including at least one of skewness, entropy, maximum between class variance, ninety nine percent index and fifty percent index.

20. The method of claim 12, wherein the method comprises obtaining the values for the predictor variables from texture features including at least one of average gradient magnitude value of the intermediate image within the region defined by the non-zero values of the ROI image, an average gradient magnitude value of the intermediate image within a subset of the region defined by the non-zero values of the ROI image, an edge ratio of the intermediate image in the region defined by the non-zero values of ROI image, and an edge ratio of the intermediate image within a subset of the region defined by the non-zero values of ROI image.

* * * * *